(12) United States Patent
Henderson

(10) Patent No.: US 9,175,345 B2
(45) Date of Patent: Nov. 3, 2015

(54) USE OF GENOMIC TESTING AND KETOGENIC COMPOUNDS FOR TREATMENT OF REDUCED COGNITIVE FUNCTION

(75) Inventor: Samuel T. Henderson, Golden, CO (US)

(73) Assignee: Accera, Inc., Broomfield, CO (US)

( * ) Notice: Subject to any disclaimer, the term of this patent is extended or adjusted under 35 U.S.C. 154(b) by 1467 days.

(21) Appl. No.: 12/671,610

(22) PCT Filed: Jul. 31, 2008

(86) PCT No.: PCT/US2008/071817
§ 371 (c)(1),
(2), (4) Date: Jun. 23, 2011

(87) PCT Pub. No.: WO2009/018478
PCT Pub. Date: Feb. 5, 2009

(65) Prior Publication Data
US 2011/0243885 A1   Oct. 6, 2011

Related U.S. Application Data

(60) Provisional application No. 60/953,074, filed on Jul. 31, 2007.

(51) Int. Cl.
*C12Q 1/68* (2006.01)
*C12P 19/34* (2006.01)

(52) U.S. Cl.
CPC ........ *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2,766,145 A | 10/1956 | Jones | |
| 2,766,146 A | 10/1956 | Ashburn | |
| 3,053,677 A | 9/1962 | Touey | |
| 4,346,107 A | 8/1982 | Cavazza et al. | |
| 4,407,821 A | 10/1983 | Mendy | |
| 4,528,197 A | 7/1985 | Blackburn | |
| 4,551,523 A | 11/1985 | Elam et al. | |
| 4,687,782 A | 8/1987 | Brantman | |
| 4,847,296 A | 7/1989 | Babayan et al. | |
| 5,093,044 A | 3/1992 | Wretlind | |
| 5,118,670 A | 6/1992 | Wurtman et al. | |
| 5,126,373 A | 6/1992 | Brunengraber et al. | |
| 5,175,190 A | 12/1992 | Burton et al. | |
| 5,276,059 A | 1/1994 | Caughey et al. | |
| 5,308,832 A | 5/1994 | Garleb et al. | |
| 5,385,915 A | 1/1995 | Buxbaum et al. | |
| 5,391,375 A | 2/1995 | Hille et al. | |
| 5,420,335 A | 5/1995 | Birkhahn et al. | |
| 5,494,794 A | 2/1996 | Wallace | |
| 5,504,072 A | 4/1996 | Schmidl et al. | |
| 5,508,167 A | 4/1996 | Roses et al. | |
| 5,538,983 A | 7/1996 | Buxbaum et al. | |
| 5,607,967 A | 3/1997 | Friedman et al. | |
| 5,614,560 A | 3/1997 | Lipton | |
| 5,650,148 A | 7/1997 | Gage et al. | |
| 5,691,325 A | 11/1997 | Sandyk | |
| 5,693,850 A | 12/1997 | Birkhahn et al. | |
| 5,716,828 A | 2/1998 | Roses et al. | |
| 5,766,621 A | 6/1998 | Trimbo et al. | |
| 5,817,626 A | 10/1998 | Findeis et al. | |
| 5,854,204 A | 12/1998 | Findeis et al. | |
| 5,854,215 A | 12/1998 | Findeis et al. | |
| 5,925,684 A | 7/1999 | Schweikert et al. | |
| 5,935,781 A | 8/1999 | Poirier | |
| 5,936,078 A | 8/1999 | Kuga et al. | |
| 5,980,939 A | 11/1999 | Kim et al. | |
| 6,027,896 A | 2/2000 | Roses et al. | |
| 6,136,862 A | 10/2000 | Hiraide et al. | |
| 6,159,942 A | 12/2000 | Cyr et al. | |
| 6,207,856 B1 | 3/2001 | Veech | |
| 6,232,345 B1 | 5/2001 | Hiraide et al. | |
| 6,316,038 B1 | 11/2001 | Veech | |
| 6,323,237 B1 | 11/2001 | Veech | |
| 6,380,244 B2 | 4/2002 | Martin | |
| 6,395,306 B1 | 5/2002 | Cui et al. | |
| 6,835,750 B1 | 12/2004 | Henderson | |
| 6,884,454 B2 | 4/2005 | Pimentel | |
| 7,001,736 B1 | 2/2006 | Poirier | |
| 7,049,078 B2 | 5/2006 | Poirier | |
| 7,087,649 B2 | 8/2006 | Barth et al. | |
| 7,622,470 B2 | 11/2009 | O'Connor et al. | |
| 7,939,530 B2 | 5/2011 | O'Connor et al. | |
| 8,124,589 B2 | 2/2012 | Henderson | |
| 8,445,535 B1 | 5/2013 | Henderson | |

(Continued)

FOREIGN PATENT DOCUMENTS

| CN | 1316902 | 10/2001 |
|---|---|---|
| CN | 1681941 | 10/2005 |

(Continued)

OTHER PUBLICATIONS

Prince et al; Human Mutation, vol. 22, pp. 363-371, 2003.*
Ertekin-Taner et al; Human Mutation, vol. 23, pp. 334-342, 2004.*
International Search Report and Written Opinion prepared by the U.S. Patent and Trademark Office as International Searching Authority (ISA/US) for PCT International Patent Application No. PCT/US2008/071817, mailed Jan. 12, 2009, 12 pages.
International Preliminary Report on Patentability prepared by the International Bureau of WIP for PCT International patent Application No. PCT/US2008/071817, mailed Feb. 11, 2010, 6 pages.

(Continued)

*Primary Examiner* — Jehanne Sitton
(74) *Attorney, Agent, or Firm* — Swanson & Bratschun, L.L.C.

(57) ABSTRACT

This invention relates to methods of using genotyping to select patients for treatment with compounds capable of elevating ketone body concentrations in amounts effective to treat reduced neuronal metabolism associated with reduced neuronal metabolism, for example Alzheimer's disease.

6 Claims, 1 Drawing Sheet

(56) References Cited

U.S. PATENT DOCUMENTS

| | | | |
|---|---|---|---|
| 8,748,400 | B2 | 6/2014 | Henderson |
| 2001/0041736 | A1 | 11/2001 | Veech |
| 2002/0006959 | A1 | 1/2002 | Henderson |
| 2002/0103139 | A1 | 8/2002 | Weisspapir et al. |
| 2003/0059824 | A1 | 3/2003 | Henderson |
| 2004/0052926 | A1 | 3/2004 | Apfelbaum |
| 2004/0058873 | A1 | 3/2004 | Esmond et al. |
| 2004/0060077 | A1 | 3/2004 | Esmond et al. |
| 2005/0009031 | A1 | 1/2005 | Becker |
| 2005/0013884 | A1 | 1/2005 | Rennels |
| 2005/0031651 | A1 | 2/2005 | Gervais et al. |
| 2005/0043242 | A1 | 2/2005 | Esmond et al. |
| 2006/0122270 | A1 | 6/2006 | Henderson |
| 2006/0134240 | A1 | 6/2006 | Miljkovic et al. |
| 2006/0189545 | A1 | 8/2006 | Henderson |
| 2006/0280721 | A1 | 12/2006 | Veech et al. |
| 2007/0066527 | A1 | 3/2007 | Tezapsidis |
| 2007/0179197 | A1 | 8/2007 | Henderson |
| 2008/0287372 | A1 | 11/2008 | Henderson |
| 2013/0005693 | A1 | 1/2013 | Henderson |
| 2014/0256808 | A1 | 9/2014 | Henderson |

FOREIGN PATENT DOCUMENTS

| | | |
|---|---|---|
| CN | 1756554 | 4/2006 |
| EP | 0 519 727 | 12/1992 |
| EP | 0443996 B1 | 6/1994 |
| EP | 0 676 205 | 10/1995 |
| EP | 0 808 626 | 11/1997 |
| EP | 1419768 A1 | 10/2001 |
| EP | 1813630 A2 | 8/2007 |
| GB | 2 368 011 | 4/2002 |
| JP | 097785 | 4/1993 |
| JP | 287138 | 11/1994 |
| JP | 2003-48831 A | 2/2003 |
| JP | 2003-531857 | 10/2003 |
| JP | 3486778 | 1/2004 |
| JP | 2006-519843 | 8/2006 |
| JP | 2007-217686 | 8/2007 |
| JP | 2008-104359 | 5/2008 |
| JP | 2009-524587 A | 7/2009 |
| WO | WO 91/15963 | 10/1991 |
| WO | WO 95/09146 | 4/1995 |
| WO | WO 96/14063 | 5/1996 |
| WO | WO 98/41200 | 9/1998 |
| WO | WO 98/41201 | 9/1998 |
| WO | WO 99/33853 | 7/1999 |
| WO | WO 99/51097 | 10/1999 |
| WO | WO 00/04895 | 2/2000 |
| WO | WO 00/15216 | 3/2000 |
| WO | WO 00/61079 | 10/2000 |
| WO | WO 01/82928 | 11/2001 |
| WO | WO 02/18400 | 3/2002 |
| WO | WO 02/053121 | 7/2002 |
| WO | WO 03-045429 | 6/2003 |
| WO | WO 2004/077938 | 9/2004 |
| WO | WO 2004/108740 | 12/2004 |
| WO | WO 2005/074970 | 8/2005 |
| WO | WO 2007/070701 | 6/2007 |
| WO | WO 2007/115282 | 10/2007 |
| WO | WO 2008/005818 | 1/2008 |
| WO | WO 2007-070701 | 11/2008 |

OTHER PUBLICATIONS

Introducing Neurontin Capsules in a New Shape Ad (1996), 1 page.
Mak et al. (1999) Acta Paediatr Sin 40(2):97-100, "Clinical Experience of Ketogenic Diet on Children with Refractory Epilepsy".
Odle (1997) American Society for Nutirtional Sciences 127:1061-1067, "New Insights into the Utilization of Medium-Chain Triglycerides by the Neonate: Observations from a Piglet Model".
Thal et al. (1996) Neurology, 47:705-711, "A 1-year multicenter placebo-controlled study of acetyl-L-carnitine in patients with Alzheimer's disease".
U.S. Appl. No. 09/845,741, filed May 1, 2001, Henderson.
U.S. Appl. No. 11/021,920, filed Dec. 22, 2004, Henderson.
Babayan (1987) Lipids, 22(6):417-420, "Specialty Lipids and Their Biofunctionality".
Bach (1996) J. Lipid Res. 37:708-726, "The usefulness of dietary medium-chain triglycerides in body weight control: fact or fancy?".
Bach et al. (1982) Amer. J. Clinic. Nutr. 36:950-962 "Medium-chain triglycerides: an update".
Beckman et al. (1998) Physiological Reviews, 78(2):547-581, "The Free Radical Theory of Aging Matures".
Beffert et al. (1998) Brain Research Reviews, 27:119-142, "The neurobiology of apolipoproteins and their receptors in the CNS and Alzheimer's disease".
Blass (2001) Journal of Neuroscience Research, 66:851-856, "Brain Metabolism and Brain Disease: Is Metabolic Deficiency the Proximate Cause of Alzheimer Dementia?".
Blass et al. (1984) Neurochem. Path., 2:103-114, "Alzheimer's Disease: A metabolic Systems Degeneration?".
Blazquez et al. (1998) J. Neurochemistry 71:1597-1606 "Role of canitine palmitoyltransferase I in the control of ketogenesis in primary cultures of rat astrocytes".
Blazquez et al. (1999) J. Neurochemistry 72:1759-1768 "The Stimulation of Ketogenesis by Cannabinoids in Cultures Astrocytes Defines Carnitine Palitoyltransferase I as a New Ceramide-Activated Enzyme".
Blazquez et al. (1999) Journal of Neurochemistry, 73:1674-1682, "The AMP-Activated Protein Kinase Is Involved in the Regulation of Ketone Body Production by Astrocytes".
Broer et al. (1997) Journal of Biological Chemistry, 272(48):30096-30102, "Comparison of Lactate Transport in Astroglial Cells and Monocarboxylate Transporter 1 (MCT 1) Expressing *Xenopus laevis* Oocytes".
Bullock (2002) British J. Psychiatry, 180:135-139, "New drugs for Alzheimer's disease and other dementias".
Corbo et al. (1999) Ann. Hum. Genet., 63:301-310, "Apolipoprotein E (APOE) allele distribution in the world. Is APOE*4 a 'thrifty' allele?".
Cox et al. (1998) J. of Pediatrics, 133(2):247-253, "Reversal of severe hypertrophic cardiomyopathy and excellent neuropsychologic outcome in very-long-chain acyl-coenzyme A dehydrogenase deficiency".
Craft et al. (1996) Neurobiology of Aging, 17(1):123-130, "Memory Improvement Following Induced Hyperinsulinemia in Alzheimer's Disease".
Cruz et al. (2001) J. Biological Chemistry, 276(15):12162-12168, "Glucose and Insulin Stimulate Heparin-releasable Lipoprotein Lipase Activity in Mouse Islets and INS-1 Cells".
Database Medline on STN (Columbus, OH, USA), No. 96063810. Bruno et al. (1995) Alzheimer Disease and Associated Disorders, "Acetyl-L-carnitine in Alzheimer disease: a short-term study on CSF neurotransmitters and neuropeptides".
Davis et al. (1999) Nature, 400:810, "Alois Alzheimer and the amyloid debate".
De Vries et al. (1997) Biochemistry, 36:5285-5292, "Functional Characterization of Mitochondrial Carnitine Palmitoyltransferases I and II Expressed in the Yeast *Pichia pastoris*".
Dewatcher et al. (2002) The Journal of Neuroscience, 22(9):3445-3453, "Neuronal Deficiency of Presenilin 1 Inhibits Amyloid Plaque Formation and Corrects Hippocampal Long-Term Potentiation But not a Cognitive Defect of Amyloid Precursor Protein [V717I] Transgenic Mice".
Dialog Results (Sep. 22, 2003) Agent for Prevention and/or therapeutics of Alzheimer's disease cont. Triglyceride of 8-10 carbon fatty acids as active ingredient, Translation of Publication No. 06-287138.
Dias (1990) Metabolism 39(9):887-891, "Effects of Medium-Chain Triglyceride Feeding on Energy Balance in Adult Human".
Edmond (1992) Can. J. Physiol. Pharmacol. 70:S118-S129, "Energy metabolism in developing brain cells".
Evans et al. (1989) JAMA, 262(18):2551-2556, "Prevalence of Alzheimer's Disease in a Community Population of Older Persons: Higher Than Previously Reported".
Extended European Search Report, prepared for European Application No. 08796988.7 by the European Patent Office, dated Jul. 30, 2010, 18 pages.

(56) References Cited

OTHER PUBLICATIONS

Finch et al. (1997) Experimental Neurology, 143:82-102, "Aging, Metabolism, and Alzheimer Disease: Review and Hypotheses".
Frolich et al. (1998) J. Neural. Transm., 105:423-438, "Brain insulin and insulin receptors in aging and sporadic Alzheimer's disease".
Gelman et al. (1999) Cell. Mol. Life Sci., 55:932-943, "An update on the mechanisms of action of the peroxisome proliferator-activated receptors (PPARs) and their roles in inflammation and cancer".
George et al. (2004) Neurobiology of Disease, 16:124-132, "APP intracellular domain is increased and soluble Aβ is reduced with diet-induced hypercholesterolemia in a transgenic mouse model of Alzheimer disease".
Goodman et al. eds. (1996) The Pharmacological Basis of Therapeutics, 8th Ed., McGraw-Hill, table of contents.
Grant (1997) Alzheimer's Disease Review, 2:42-55, "Dietary Links to Alzheimer's Disease".
Greenberg et al. (2000) Arch. Neurol. 57:94-99, "Donepezil Therapy in Clinical Practice: A Randomized Crossover Study".
Gregg et al. (1986) The Journal of Clinical Investigation, Inc. 78:815-821 "Abnormal in Vivo Metabolism of Apolipoprotein E4 in Humans".
Guillot et al. (1993) Brit. J. of Nutri. 69(2):431-442 "Intestinal absorption and liver uptake of medium-chain fatty acids in non-anaesthetized pigs".
Guzman et al. (2001) Trends in Endocrinology and Metabolism, 12(4):169-173, "Is there an astrocyte-neuron ketone body shuttle?".
Haan et al. (2004) Annu. Rev. Public Health, 25:1-24, "Can Dementia Be Prevented? Brain Aging in a Population-Based Context".
Halestrap et al. (1999) Biochem J., 343:281-299, "The proton-linked monocarboxylate transporter (MCT) family: structure, function and regulation".
Hall et al. (1998) Australian and New Zealand Journal of Psychiatry, 32:698-706, "Risk factors and Alzheimer's disease: a comparative study of two communities".
Hamosh (1990) In: Lingual and Gastric Lipases: Their Role in Fat Digestion. CRC press.
Hanlon et al. (1995) Atherosclerosis, 112:85-90, "Arginine residues at codons 112 and 158 in the apolipoprotein E gene correspond to the ancestral state in humans".
Hasselbalch et al. (1996) Cerebral Metabolism and Blood Flow in Hyperketonemia, E746-E751, "Changes in cerebral blood flow and carbohydrate metabolism during acute hyperketonemia".
Hayes (2000) Am. J. Clin. Nutr. (2000) 72:1583-1593, "Medium-chain triacylglycerols may not raise cholesterol".
Henderson (2004) Medical Hypotheses, 62:689-700, "High carbohydrate diets and Alzheimer's disease".
Hertz et al. (2000) Neurochemistry International, 37:83-102, "Neuronal-astrocytic and cytosolic-mitochondrial metabolite trafficking during brain activation, hyperammonemia and energy deprivation".
Ho et al. (2004) FASEB Journal, 18:902-904, "Diet-induced insulin resistance promotes amyloidosis in a transgeneic mouse model of Alzheimer's disease".
Hoyer (1992) Mol. Chem. Neuropathol., 16:207-224, "Oxidative Energy Metabolism in Alzheimer Brain: Studies in Early-Onset and Late-Onset Cases".
Hoyer (1998) J. Neural Transm., 105:415-422, "Is sporadic Alzheimer disease the brain type of non-insulin dependent diabetes mellitus? A challenging hypothesis".
Huff et al. (1987) J. Lipid Res., 28:1118-1123, "Separation and isolation of human apolipoproteins CII, C-III0, C-III1, and C-III2 by chromatofocusing on the Fast Protein Liquid Chromatography system".
Huttenlocher (1976) Pediatric Research, 10:536-540, "Ketonemia and Seizures: Metabolic and Anticonvulsant Effects of Two Ketogenic Diets in Childhood Epilepsy".
Jandacek et al. (1978) Chemistry and Physics of Lipids, 22:163-176, "Physical properties of pure sucrose octaesters".
Johnson et al. (1999) International Journal of Epidemiology, 28:1102-1109, "Adult nutrient intake as a risk factor for Parkinson's disease".
Jolles et al. (1992) Journal of Neurochemistry, 58(6):2326-2329, "Phosphatidylinositol Kinase Is Reduced in Alzheimer's Disease".
Jong et al. (1999) Arterioscler. Thromb. Vasc. Biol., 19:472-484, "Role of ApoCs in Lipoprotein Metabolism: Functional Differences Between ApoC1, ApoC2, and ApoC3".
Kalmijn et al. (1997) Annals of Neurology, 42(5):776-782, "Dietary Fat Intake and the Risk of Incident Dementia in the Rotterdam Study".
Kashiwaya et al. (2000) PNAS USA, 97(10):5440-5444, "D-β-Hydroxybutyrate protects neurons in models of Alzheimer's and Parkinson's disease".
Kimball et al. (2002) J. Appl. Physiol., 93:1168-1180, "Exercise Effects on Muscle Insulin Signaling and Action. Invited Review: Role of insulin in translational control of protein synthesis in skeletal muscle by amino acids or exercise".
Klivenyi et al. (1999) Nature Medicine, 5(3):347-350, "Neuroprotective effects of creatine in a transgenic animal model of amyotrophic lateral sclerosis".
Knouff et al. (1999) The Journal of Clinical Investigation, 103(11):1579-1586, "Apo E structure determines VLDL clearance and atherosclerosis risk in mice".
Kolanowski et al. (1994) Metabolism, 43(2):180-185, "Stimulatory Influence of D(-)3-Hydroxybutyrate Feeding on Sympathetic Nervous System Activity in the Rat".
Koo et al. (1999) PNAS USA, 96:9989-9990, "Amyloid diseases: Abnormal protein aggregation in neurodegeneration".
Kudo et al. (1995) J. of Biological Chemistry, 270(29):17513-17520, "High Rates of Fatty Acid Oxidation during Reperfusion of Ischemic Hearts are Associated with a Decrease in Malonyl-CoA Levels Due to an Increase in 5'-AMP-activated Protein Kinase Inhibition of Acetyl-CoA Carboxylase".
Lannert et al. (1998) Behavioral Neuroscience, 112(5):1199-1208, "Intracerebroventricular Administration of Streptozotocin Causes Long-Term Diminutions in Learning and Memory Abilities and in Cerebral Energy Metabolism in Adult Rats".
Lefevre et al. (2000) Pediatrics, 105:E46, "Ketogenic Diet for the Treatment of Refractory Epilepsy in Children: A Systematic Review of Efficacy".
Leino et al. (2001) Neurochemistry International, 38:519-527, "Diet-induced ketosis increases monocarboxylate transporter (MCT1) levels in rat brain".
Ling et al. (2001) J. Med. Chem., 44:3141-3149, "Identification of Alkylidene Hydrazides as Glucagon Receptor Antagonists".
Liu et al. (2002) Am. J. Physiol. Endo. Metab., 283:E1105-E1112, "Human protein metabolism: its measurement and regulation".
Loktionov et al. (1999) Atherosclerosis, 145:125-135, "Apolipoprotein E and methylenetetrahydrofolate reductase genetic polymorphisms in relation to other risk factors for cardiovascular disease in UK Caucasians and Black South Africans".
Mahley et al. (1999) J. Lipid Research, 40:1933-1949, "Pathogenesis of type III hyperlipoproteinemia (dysbetalipoproteinemia): questions, quandries, and paradoxes".
Mattson (1998) Science and Medicine, Mar./Apr. 17-25, "Experimental Models of Alzheimer's Disease".
McKhann et al (1984) Neurology, 34:939-943, "Clinical diagnosis of Alzheimer's disease: Report of the NINCDS-ADRDA Work Group under the auspices of Department of Health and Human Services Task Force on Alzheimer's Disease".
Meier-Ruge et al. (1994) Gerontology, 40:246-252, "Changes in Brain Glucose Metabolism as a Key to the Pathogenesis of Alzheimer's Disease".
Messier et al. (1996) Behavioural Brain Research, 75:1-11, "Glucose regulation and cognitive functions: relation to Alzheimer's deases and diabetes".
Michalik et al. (2003) Human Molecular Genetics, 12:R173-186, "Pathogenesis of polyglutamine disorders: aggregation revisited".
Mitchell et al. (1995) Clin. Invest. Med. 18:3, 193-216 "Medical aspects of ketone body metabolism".

(56) References Cited

OTHER PUBLICATIONS

Moechars et al. (1999) J. Biological Chemistry, 274(10):6483-6492, "Early Phenotypic Changes in Transgenic Mice That Overexpress Different Mutants of Amyloid Precursor Protein in Brain".
Morris et al. (2003) Arch. Neurol., 60:194-200, "Dietary Fats and the Risk of Incident Alzheimer Disease".
Murray et al. (1999) Harper's Biochemistry, 25th ed.:927.
Nadal et al. (2002) Biochem. J., 366:289-297, "Down-regulation of the mitochondrial 3-hydroxy-3-methylglutaryl-CoA synthase gene by insulin: the role of the forkhead transcription factor FKHRL1".
Nebeling et al. (1995) J. Am. Diet Assoc., 95(6):693-697, "Implementing a ketogenic diet based on medium-chain triglyceride oil in pediatric patients with cancer".
Neve et al. (1998) Trends Neurosci., 21:15-19, "Alzheimer's disease: a re-examination of the amyloid hypothesis".
Nishimura et al. (1999) Clin. Genet., 55:219-225, "Biology of presenilins as causative molecules for Alzheimer disease".
Nordberg (2004) Lancet Neurol., 3:519-527, "PET imaging of amyloid in Alzheimer's disease".
Notice of Opposition sent Dec. 28, 2009 by the European Patent Office for 01930965.7, 19 pages.
Ogawa et al. (1996) Journal of the Neurological Sciences, 139:78-82, "Altered energy metabolism in Alzheirmer's disease".
Osuntokun et al. (1995) Ann. Neurol., 38:463-465, "Lack of an Association Between apolipoprotein E ϵ4 and Alzheimer's Disease in Elderly Nigerians".
Pegorier et al. (1988) Biochem Journal 249:801-806, "Fatty acid metabolism in hepatocytes isolates from rats adapted to high-fat diets containing long- or medium-chain triacylglycerols".
Pettegrew et al. (2000) Molecular Psychiatry 5:616-632 "Acetyl-L-carnitine physical-chemical, metabolic, and therapeutic properties; relevance for its mode of action in Alzheimer's disease and geriatric depression".
Pi-Sunyer et al. (Feb. 1969) Diabetes, 18(2):96-100, "Insulin and Ketone Responses to Ingestion of Medium and Long-chain Triglycerides in Man".
Poirier et al. (1995) PNAS USA 92:12260-12264, "Apolipoprotein E4 allele as a predictor of cholinergic deficits and treatment outcome in Alzheimer disease".
Qureshi et al. (2000) J. Biological Chemistry, 275(47):36590-36595, "Activation of Insulin Signal Transduction Pathway and Anti-diabetic Activity of Small Molecule Insulin Receptor Activators".
Refolo et al. (2000) Neurobiology of Disease, 7:321-331, "Hypercholesterolemia Accelerates the Alzheimer's Amyloid Pathology in a Transgenic Mouse Model".
Reiman et al. (1996) The New England Journal of Medicine, 334:752-758, "Preclinical Evidence of Alzheimer's Disease in Persons Homozygous for the ϵ4 Allele for Apolipoprotein E".
Robinson et al. (2004) Neurobiology of Aging, 25:609-615, Lessons from the AN 1792 Alzheimer vaccine: lest we forget.
Roheim et al. (1979) PNAS USA, 76(9):4646-4649, "Apolipoproteins in human cerebrospinal fluid".
Sato et al. (2003) Exp. Biol. Med., 228:1208-1212, "Physical Exercise Improves Glucose Metabolism in Lifestyle-Related Diseases".
Schenk et al. (1999) Nature, 400:173-177, "Immunization with amyloid-β attenuates Alzheimer-disease-like pathology in the PDAPP mouse".
Schoonjans et al. (1999) FEBS Letters, 452:160-164, "3-Hydroxy-3-methylglutaryl CoA reductase inhibitors reduce serum triglyceride levels through modulation of apolipoprotein C-III and lipoprotein lipase".
Selkoe (1994) Journal of Neuropathology and Experimental Neurology, 53(5):438-447, "Alzheimer's Disease: A Central Role for Amyloid".
Selkoe (1999) Nature Supplement, 399:A23-31, "Translating cell biology into therapeutic advances in Alzheimer's disease".
Selkoe (2001) Physiological Reviews, 81(2):741-766, "Alzheimers's Disease: Genes, Proteins, and Therapy".
Selkoe (2004) Ann. Intern. Med., 140:627-638, "Alzheimer Disease: Mechanistic Understanding Predicts Novel Therapies".
Shah et al. (2000) Am. J. Physiol. Endocrinol. Metab., 279:E715-E729, "4E-BP1 and S6K1: translational integration sites for nutritional and hormonal information in muscle".
Shi et al. (1999) J. Biological Chemistry, 274(14):9421-9426, "A Single Amino Acid Change (Substitution of Glutamate 3 with Alanine) in the N-terminal Region of Rat Liver Carnitine Palmitoyltransferase I Abolishes Malonyl-CoA Inhibition and High Affinity Binding".
Shie et al. (2002) Neuroreport, 13:455-459, "Diet-induced hypercholesterolemia enhances brain A beta accumulation in transgenic mice.".
Simpson et al. (1994) Ann. Neurol., 36:800-801, Reduced Glucose Transporter Concentrations in Brains of Patients with Alzheimer's Disease.
Sirven et al. (1999) Epilepsia, 40(12):1721-1726, "The Ketogenic Diet for Intractable Epilepsy in Adults: Preliminary Results".
Staels et al. (1998) Circulation, 98(19):2088-2093, "Mechanism of Action of Fibrates on Lipid and Lipoprotein Metabolism".
Stokin et al. (2005) Science, 307:1282-1288, "Axonopathy and Transport Deficits Early in the Pathogenesis of Alzheimer's Disease".
Strittmatter et al. (1996) Annu. Rev. Neurosci., 19:53-77, "Apolipoprotein E and Alzheimer's Disease".
Sugiura et al. (1996) Biochemical and Biophysical Research Communications, 229:58-64, "2-Arachidonoylglycerol, a Putative Endogenous Cannabinoid Receptor Ligand, Induces Rapid, Transient Elevation of Intracellular Free Ca2+ in Neuroblastoma X Glioma Hybrid NG108-15 Cells".
Sugiura et al. (1997) J. Biochem., 122:890-895, "Is the Cannabinoid CB1 Receptor a 2-Arachidonoylglycerol Receptor? Structural Requirements for Triggering a Ca2+ Transient in NG108-15 Cells".
Sugiura et al. (1999) J. Biological Chemistry, 274(5):2794-2801, "Evidence That the Cannabinoid CB1 Receptor Is a 2-Arachidonoylglycerol Receptor".
Sugiura et al. (2000) J. Biological Chemistry, 275(1):605-612, "Evidence That 2-Arachidonoylglycerol but Not N-Palmitoylethanolamine or anandamide Is the Physiological Ligand for the Cannabinoid CB2 Receptor".
Swaab et al. (1998) Progress in Brain Research, 117:343-377, "Reduced neuronal activity and reactivation in Alzheimer's disease".
Takada et al. (1991) Bull. Inst. Chem. Res., 69(2):77-83, "Preparation of Cellobiose Octa(n-alkanoate)s and Their Thermal Properties".
Takada et al. (1992) Liquid Crystals, 12(2):337-345, "Columnar liquid crystals in oligosaccharide derivatives: II. Two types of discotic columnar liquid-crstalline phase of cellobiose alkanoates".
Takada et al. (1995) Liquid Crystals, 19(4):441-448, "Discotic columnar liquid crystals in oligosaccharide derivatives: III. Anomeric effects on the thermo-mesomorphic properties of cellobiose octa-alkanoates".
Taylor et al. (2002) Science, 296:1991-1995, "Toxic Proteins in Neurodegenerative Disease".
Thavendiranathan et al. (2000) Experimental Neurology, 161:696-703, "The MCT Ketogenic Diet: Effects on Animal Seizure Models".
U.S. Appl. No. 11/331,673, Office Action dated Oct. 10, 2008, 30 pages.
Van Dyck et al. (1998) Arch. Neurol., 55:1460-1466, "Absence of an Apolipoprotein E ϵ4 Allele Is Associated With Increased Parietal Regional Cerebral Blood Flow Asymmetry in Alzheimer Disease".
Van Wymlbeke (2001) Am. J. Clin. Nut. 74:620-630, "Substrate oxidation and control of food intake in men after a fat-substitute meal compared with meals supplemented with an isoenergetic load of carbohydrate, long-chain triacylglycerols, or medium-chain triacylglycerols".
Veech et al. (2001) IUBMB Life, 51:241-247, "Ketone Bodies, Potential Therapeutic Uses".
Veneman et al. (1994) Diabetes, 43:1311-1317, "Effect of Hyperketonemia and Hyperlacticacidemia on Symptoms, Cognitive Dysfunction, and Counterregulatory Hormone Responses During Hypoglycemia in Normal Humans".
Wang et al. (2000) J. Biological Chemistry, 275(27):20782-20786, "Abnormal Sodium Stimulation of Carnitine Transport in Primary Carnitine Deficiency".

(56) References Cited

OTHER PUBLICATIONS

Wang et al. (2005) FASEB Journal, 19:659-661, "Caloric restriction attenuates (β-amyloid neuropathology in a mouse model of Alzheimer's disease".
Winocur et al. (1999) Behavioural Brain Research, 101:153-161, "The effects of high fat diets and environmental influences on cognitive performance in rats".
Witters et al. (1988) PNAS, USA, 85:5473-5477, "Insulin stimulates the dephosphorylation and activation of acetyl-CoA carboxylase".
Wu et al. (2003) Neuroscience, 119:365-375, "A Saturated-fat Diet Aggravates the Outcome of Traumatic Brain Injury on Hippocampal Plasticity and Cognitive Function by Reducing Brain-derived Neurotrophic Factor".
Yamamoto et al. (2000) Cell, 101:57-66, "Reversal of Neuropathology and Motor Dysfunction in a Conditional Model of Huntington's Disease".
York et al. (1997) Carb. Research, 300:199-206, "Determination of the absolute configuration of monosaccharides by $^1$H NMR spectroscopy of their per-0-(S)-2-methylbutyrate derivatives".
Zekraoui et al. (1997) Human Biology, 69(4):575-577, "High frequency of the apolipoprotein E *4 allele in African pygmies and most of the African populations in Sub-Saharan Africa".
Zhao et al (2004) Pediatric Research, 55(3):498-506, "Detrimental Effects of the Ketogenic Diet on Cognitive Function in Rats".
Zhou et al. (1998) Molecular Endocrinology, 12:1594-1604, "Nuclear Receptors Have Distinct Affinities for Coactivators: Characterization by Fluorescence Resonance Energy Transfer".
Zief (1950) J. of Amer. Chem. Soc. 72:1137-1140, "Unsaturated Esters of Sucrose".
Zubenko et al. (1999) Biol. Psychiatry, 45:731-736, "Reductions in Brain Phosphatidylinositol Kinase Activities in Alzheimer's Disease".
Messier et al., "The Role of Insulin, Insulin Growth Factor, and Insulin-Degrading Enzyme in Brain Aging and Alzheimer's Disease", 2005, Neural Plasticity, vol. 12, No. 4, pp. 311-328.
Reger et al. (2004) Neurobiology of Aging, 25:311-314, "Effects of β-hydroxybutyrate on cognition in memory-impaired adults".
Notice of Opposition sent Dec. 28, 2009 by the European Patent Office for 01930965.7.
BMC Medical Genetics, 2011, vol. 12, Article 137.
BMC Medical Genetics, 2011, vol. 12, Article 151.
Edland et al. (2003) *Neuroscience Letters* 345 p. 21-24 "Insulin degrading enzyme (IDE) genetic variants and risk of Alzheimer's disease: evidence of effect".
Experimental Drug Ketasyn™ (AC-1202) Treats Alzheimer's As Diabetes of the Brain, medicalnewstoday.com URL: http://www.medicalnewstoday.com/printerfriendlynews.php?newsid=75335.
Grupe et al. (2006) *Am J of Human Genetics* 78 p. 78-88 "A scan of chromosome 10 identifies a novel locus showing strong association with late-onset Alzheimer disease".
Henderson et al. (2009) *Nutrition & Metabolism* 6:31 "Study of the ketogenic agent AC-1202 in mild to moderate Alzheimer's disease".
Risner et al. (2006) *Pharmacogenomics* J 6 p. 246-254 "Efficacy of rosiglitazone in a genetically defined population with mild-to-moderate Alzheimer's disease".
Wegman et al. (2005) *Breast Cancer Research* 7 p. R284-R290 "Genotype of metabolic enzymes and the benefit of tamoxifen in postmenopausal breast cancer patients".
Article World "human weight" also available at http://www.articleworld.org/index.php?title=Human_weight&printable=yes; last viewed Apr. 6, 2010.
Australian Examination Report for Application No. 2009266869 dated Sep. 30, 2014.
Birkhahn et al. (1986) Journal of Nutrition 116:851-864 "Total Parenteral Feeding of Rats with an Acetoacetate Monoglyceride and Glucose Mixture".
Birkhahn et al. (1994) Journal of Parenteral and Enteral Nutrition 18(3):219-224 "Parenteral Monoacetoacetin and Liver Regeneration Interaction After Partial Hepatectomy in the Rat".

Brosnan and Brosnan (2006) Journal of Nutrition 136(1):207S-211S "Branched-Chain Amino Acids: Metabolism, Physiological Function, and Application".
Bruno et al. (1995) Alzheimer Disease and Associated Disorders 3:128-131 "Acetyl-L-Carnitine in Alzheimer disease: a short-term study on CSF neurotransmitters and neuropeptides".
Crook et al. (1986) Developmental Neuropsychology 2(4):261-276 "Age-associated memory impairment: Proposed diagnostic criteria and measures of clinical change—report of a national institute of mental health work group".
DeCarli (2003) The Lancet Neurology 2:15-21 "Mild cognitive impairment: prevalence, prognosis, aetiology, and treatment".
Ettmayer et al. (2004) Journal of Medicinal Chemistry 47(10):2393-2404 "Lessons Learned from Marketed and Investigational Prodrugs".
Fratiglioni et al. (1991) Neurology 41:1886-1892 "Prevalence of Alzheimer's disease and other dementias in an elderly urban population: Relationship with age, sex, and education".
Freeman et al. (2006) Epilepsy Research 68:145-180 "The ketogenic diet: From molecular mechanisms to clinical effects".
Hashim et al. (2014) "Ketone Body Therapy: From the Ketogenic Diet to the Oral Administration of Ketone Ester" J of Lipid Research pp. 1-35.
Hiroyuki et al. Machine Translation of JP 06-287138, obtained Apr. 6, 2010, 9 pages.
Hänninen (1996) Neurologian klinikan julkaisusarja 39:1-34 "Age-Associated Memory Impairment".
International Search Report and Written Opinion for PCT/US09/49605 mailed Aug. 14, 2009, 10 pages.
Jankovic and Aguilar (2008) Neuropsychiatric Disease and Treatment 4(4):743-757 "Currrent approaches to the treatment of Parkinson's disease".
Japanese Office Action for Application No. 2010-520202 dated Mar. 4, 2014.
Japanese Office Action for Application No. 2011-516888 dated Feb. 5, 2014.
Japanese Office Action for Application No. 2012-267035 dated Feb. 21, 2014.
Kalaria et al. (1992) Annals of Neurology 32(4):583-586 "Carnitine Acetyltransferase Activity in the Human Brain and Its Microvessels is Decreased in Alzheimer's Disease".
Karmee et al., (2005) "Rapid and Simple Method of Monoacylation of Polyols by β-Ketoesters Using Microwave Irradiation" Synthetic Communications, 35: 1151-1160.
Kidd (2008) Alternative Medicine Review 13(2):85-115 "Alzheimer's Disease, Amnestic Mild Cognitive Impairment, and Age-Associated Memory Impairment: Current Understanding and Progress Toward Integrative Prevention".
Ko and Lee (1999) Gastroenterology Clinics 28(1):100-116 "Bile Salts: Metabolic Pathologic, and Therapeutic Considerations".
Lambert et al. (2005) J Neural Neurosurg Psychiatry 76:928-933 "Is there a relation between APOE expression and brain amyloid load in Alzheimer's disease?".
Leadbeater et al., (2007) "Probing the effects of microwave irradiation on enzyme-catalysed organic transformations: the case of lipase-catalysed transesterification reactions", Org & Biomolecular Chem, 5;7: 1052-1055.
Loveman et al. (2006) Health Technology Assessment 10(1)1-375 "The Clinical and cost effectiveness of donepezil, rivastigmine, galantamine and memantine for Alzheimer's disease".
Nagayama and Birkhahn (1987) Japanese Journal of Surgical Metabolism and Nutrition 20:393-399 "Intravenous Tolerance Test of new Synthetic Energy Source (monoacetoacetin: MA in Rats".
Nagayama and Birkhahn (1987) The Japanese Journal of Gastroenterological Surgery 20(5):1087-1092 "Effect to Colonic Anastomosis in Postoperative TPN with Monoacetoacetin as New Synthetic Energy Source in Rats".
Nagayama et al. (1990) Japanese Journal of Surgical Metabolism and Nutrition 24:521529 "Enteral Nutrition with Monoacetoacetin as an Energy and Ketone Body Sources in Rats".
Nishiguchi et al. (2001) The Japanese Journal of Parenteral and Enteral Nutrition 23(6):327-332 "Clinical aspect of nutritional therapy using ketone body".

(56) References Cited

OTHER PUBLICATIONS

Nutrition Data "Seeds, sunflower seed kernels, toasted, without salt" (one ounce); also available at http://www.nutritiondata.com/facts/nut-and-seed-products/3079/2; last viewed Apr. 6, 2010.

Ogden et al. (2004) Advance Data from Vital and Health Statistics 347:1-18 "Mean Body Weight, Height, and Body Mass Index, United States 1960-2002".

Rocca et al. (1991) Annals of Neurology 30(3):381-390 "Frequency and distribution of alzheimer's disease in Europe: A collaborative study of 1980-1990 prevalence findings".

Small et al. (2000) Proc. Natl. Acad. Sci. 97(11):6037-6042 "Cerebral metabolic and cognitive decline in persons at genetic risk for Alzheimer's disease".

Stella (2004) Expert Opin. Ther. Patents 14(3):277-280 "Prodrugs as therapeutics".

Testa (2004) Biochemical Pharmacology 68:2097-2106 "Prodrug research: futile or fertile?".

van Dongen et al. (2000) J Am Geriatr Soc. 48(10):1183-1194 "The efficacy of ginkgo for elderly people with dementia and age-associated memory impairment: new results of a randomized clinical trial".

Wolff (1995) Burger's Medicinal Chemistry and Drug Discovery Fifth Edition, vol. 1:975-977 "Principles and Practice".

Yadav et al. (2004) "Synergism between microwave and enzyme catalysis in intensification of reactions and selectivities: transesterification of methyl acetoacetate with alcohols" J. Molecular Catalysis A: Chem 223; 1-2: 51-56.

Yadav et al. (2005) "Lipase catalyzed transesterification of methyl acetoacetate with η-butanol", J. Molecular Catalysis B: Enzymatic 32: 107-113.

McGleenon, B. M. et al. (1999) "Acetylcholinesterase inhibitors in Alzheimer's disease" J. Clin. Pharmacol, 48:471-480.

Prince et al. (2003) "Genetic Variation in a Haplotype Block Spanning IDS Influences Alzheimer Disease" Human Mutation, 22:363-371.

Ertekin-Taner et al. (2004) "Genetic Variants in a Haplotype Block Spanning IDS Are Significantly Associated with Plasma Aβ42 Levels and Risk for Alzheimer Disease" Human Mutation, 23:334-342.

\* cited by examiner

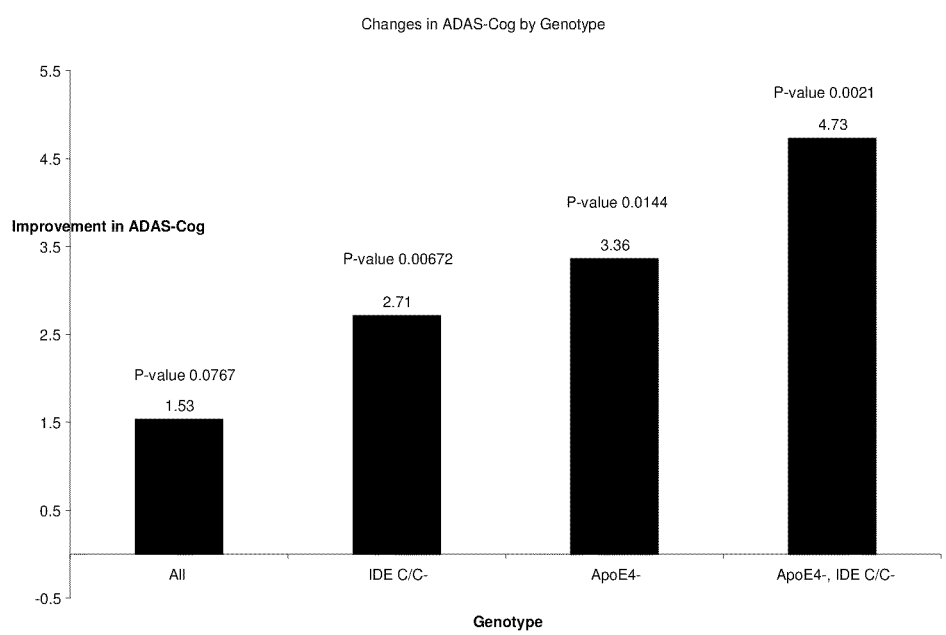

USE OF GENOMIC TESTING AND KETOGENIC COMPOUNDS FOR TREATMENT OF REDUCED COGNITIVE FUNCTION

CROSS-REFERENCE TO RELATED APPLICATIONS

This application is a 35 USC §371 of PCT Application Serial No. PCT/US2008/071817, filed Jul. 31, 2008, currently pending, entitled "Use of Genomic Testing and Ketogenic Compounds for Treatment of Reduced Cognitive Function," which claims priority to U.S. Provisional Patent Application No. 60/953,074, filed Jul. 31, 2007, entitled "Genomic testing in Alzheimer's disease and other diseases associated with reduced neuronal metabolism," which are each incorporated herein in their entirety by reference.

FIELD OF THE INVENTION

This invention relates to methods of selecting patients for a treatment for reduced cognitive function, wherein the treatment comprises administering to the patient at least one compound capable of elevating ketone body concentrations in an amount effective for the treatment of reduced cognitive function. Reduced cognitive function is associated with Age-Associated Memory Impairment (AAMI), Alzheimer's Disease (AD), Parkinson's Disease, Friedreich's Ataxia (FRDA), GLUT1-deficient Epilepsy, Leprechaunism, and Rabson-Mendenhall Syndrome, Coronary Arterial Bypass Graft (CABG) dementia, anesthesia-induced memory loss, Huntington's Disease, and many others.

Incorporated by reference herein in its entirety is the Sequence Listing co-submitted with the instant application, entitled "SeqListing ST25.txt", created Jul. 31, 2008, size of 11.7 kilobytes.

BACKGROUND OF THE INVENTION

Alzheimer's Disease

Alzheimer's disease (AD) is a progressive neurodegenerative disorder that primarily affects the elderly. In 1984, Blass and Zemcov (Blass and Zemcov 1984) proposed that AD resulted from a decreased metabolic rate in sub-populations of cholinergic neurons. Measurements of cerebral glucose metabolism indicate that glucose metabolism is reduced 20-40% in AD resulting in critically low levels of ATP.

Attempts to compensate for reduced cerebral metabolic rates in AD have met with some success. Elevation of serum ketone body levels in AD patients raises cognitive scores (Reger, Henderson et al. 2004) and USP.

Parkinson Disease (PD)

Parkinson's disease (PD) is a progressive neurodegenerative disorder that is the second most common neurodegenerative disease after Alzheimer's disease. The estimated prevalence of PD is 0.3 percent in the general U.S. population and a prevalence of 4 to 5 percent in those older than 85 years. PD is characterized by motor abnormalities, including tremors, muscle stiffness, lack of voluntary movements, and postural instability. A primary neuropathological feature of PD is the loss of dopaminergic neurons in the substantia nigra pars compacta (SNpc) and the presence of eosinophilic intracytoplasmic inclusions (Lewy bodies) in the residual dopaminergic neurons.

Therefore, there exists a need for more effective treatments for PD and in particular for treatments that are neuroprotective.

While the cause of sporadic PD is uncertain, several lines of evidence suggest that defects in oxidative phosphorylation may contribute to its pathogenesis. For example, 1-methyl-4-phenyl-1,2,3,6-tetrahydropyridine (MPTP), blocks complex I (NADH-ubiquinone oxidoreductase) of the mitochondrial electron transport chain, and causes the loss of dopaminergic neurons and the typical symptoms of PD. Reduction in complex I activity has also been reported in PD tissues. This defect is not confined only to the brain but has also been found in platelets from PD patients.

D-beta-Hydroxybutyrate (BHB) is a ketone body produced by hepatocytes and, to a lesser extent, by astrocytes. BHB acts as an alternative source of energy in the brain when glucose supply is limited such as during starvation. BHB has been found to protect from MPTP-related complex I inhibition, by enhancing oxidative phosphorylation (Tieu, 2003).

Friedreich's Ataxia (FRDA)

FRDA is a recessive disease characterized by progressive ataxia, hypertrophic cardiomyopathy, early onset of insulin-resistant diabetes, invalidism, and premature death. FRDA is a genetic disorder caused by a deficiency of frataxin, a 210 amino acid nuclear-encoded mitochondrial protein. Low levels of the protein are due to the expansion of an intronic GAA repeat, leading to decreased mRNA levels. FRDA patients show a decrease in the activity of the mitochondrial enzyme aconitase. Aconitase is responsible for conversion of citrate to isocitrate, the first step in the Krebs (also known as the citric acid or TCA cycle). Deficiency of frataxin in human patients is thought to lead primarily to defects in the TCA cycle.

Recent work shows that elevation of blood ketone bodies, a normal response to fasting, can increase mitochondrial citrate and isocitrate levels, thus overcoming the block in aconitase found in FRDA. A ketone body-based therapy could provide an effective treatment for this group of patients.

GLUT1-deficient Epilepsy

GLUT1-deficient Epilepsy is characterized by infantile seizures, delayed development, and acquired microcephaly with mental retardation. GLUT1-deficient epilepsy results from several types of mutation in the gene of GLUT1. Glucose transporter 1 (GLUT1) is the major protein responsible for the transport of glucose from bloodstream into the brain. Under standard dietary conditions, the brain is almost entirely dependent upon blood glucose for energy. However, under some circumstances, such as starvation, ketone bodies can provide a source of energy different from glucose. Ketone bodies do not rely on GLUT1 for transport into the brain and therefore may provide energy in GLUT1-deficient syndrome. Ketone body therapy may therefore become a practical method for lifelong treatment of these patients.

Leprechaunism and Rabson-Mendenhall Syndrome

Leprechaunism and Rabson-Mendenhall syndrome are rare disease characterized by insulin resistance, persistent hyperglycemia and retardation of growth. Subjects rarely survive past 20 years of age. These syndromes result from mutations in the insulin receptor gene, which lower the receptors affinity for insulin. The current treatment consists of administration of increasing doses of insulin (up to several thousand units per day). This treatment yields only weak results due to the poor binding of insulin to its receptor. Ketone bodies have been shown to mimic the effects of insulin's stimulation of the PDH multienzyme complex, thereby increasing the Krebs TCA cycle metabolite levels, increasing the energy output in the form of ATP, and enhancing metabolic efficiency. A ketone-rich, or ketogenic diet may prove an effective treatment of these conditions.

Age-Associated Memory Impairment

Aging causes deterioration of various aspects of physiology in normal adults, including memory performance. Such age related declines in cognitive performance have long been recognized by medical practitioners. Impairment of memory performance in the elderly has been detected in several standard memory tests, including the Wechsler Memory Scale (WMS) and immediate and delayed Visual Reproduction Test (Trahan et al. Neuropsychology, 1988 19(3) p. 173-89), the Rey Auditory Verbal Learning Test (RAVLT) (Ivnik, R. J. et al. Psychological Assessment: A Journal of Consulting and Clinical Psychology, 1990 (2): p. 304-312) and others (for review see Larrabee and Crook, Int. Psychogeriatr, 1994 6(1): p. 95-104.

Other Diseases and Syndromes

A great number of other diseases and syndromes are associated with decreased metabolism. Such conditions include Coronary Arterial Bypass Graft (CABG) dementia, anesthesia induced memory loss, Huntington's disease and many other. It is apparent that a metabolic intervention may aid people suffering from such afflictions.

There is thus a need in the art to develop compositions and methods for the treatment and/or prevention of cognitive impairment, particularly in aging or geriatric mammals such as humans.

Various publications, including patents, published applications, technical articles and scholarly articles are cited throughout the specification. Each of these cited publications is incorporated by reference herein, in its entirety. A partial list of those patents and applications referenced herein include, for example, U.S. Ser. No. 60/953,074, "Genomic testing in Alzheimer's disease and other diseases associated with reduced neuronal metabolism", filed Jul. 31, 2007; U.S. Ser. No. 60/917,886, "Inhibitors of Acetyl-CoA Carboxylase for Treatment of Hypometabolism", filed May 14, 2007; U.S. Ser. No. 11/123,706, "Method for Reducing Levels of Disease Associated Proteins", filed May 3, 2005; U.S. Ser. No. 11/424,429, "Method To Reduce Oxidative Damage And Improve Mitochondrial Efficiency", filed Jun. 15, 2006; U.S. Ser. No. 10/546,976, "Novel-Chemical Entities and Methods for their Use in Treatment of Metabolic Disorders", filed Aug. 25, 2005; U.S. Ser. No. 09/845,741, filed May 1, 2001; U.S. Ser. No. 10/152,147, filed Dec. 28, 2004, now U.S. Pat. No. 6,835,750; U.S. Ser. No. 11/021,920, filed Dec. 22, 2004; U.S. Ser. No. 11/331,673, filed Jan. 13, 2006; U.S. Ser. No. 11/611,114, filed Dec. 14, 2006; and U.S. Ser. No. 11/771,431, filed Jun. 29, 2007.

SUMMARY OF THE INVENTION

In one embodiment, the invention comprises a method of selecting a patient having, or at risk of having reduced cognitive function caused by reduced neuronal metabolism, determining in the patient the presence of at least one of the specific genotypes including: heterozygosity for C/T for Insulin Degrading Enzyme (IDE) rs2551101 at relevant portion shown by SEQ ID NO:3, absence of homozygosity for C/C of IDE rs2551101 at relevant portion shown by SEQ ID NO:3, heterozygosity for A/C of Apolipoprotein E (APOE) rs405509 at relevant portion shown by SEQ ID NO:21, heterozygosity for G/A of Butyrylcholine esterase (BUCHE) rs1803274 at relevant portion shown by SEQ ID NO:18, homozygosity for adenine of Insulin-like Growth Factor Receptor precursor (IGF1R) rs2229765 at relevant portion shown by SEQ ID NO:6, homozygosity for thymine of Interleukin-1 beta (IL1B) rs1143627 at relevant portion shown by SEQ ID NO:9, homozygosity for cytosine of IL rs16944 at relevant portion shown by SEQ ID NO:10, homozygosity for cytosine of Low-density Lipoprotein Receptor (LDLR) rs2738447 at relevant portion shown by SEQ ID NO:24, homozygosity for guanine of LDLR rs7259278 at relevant portion shown by SEQ ID NO:25, and homozygosity for cytosine of LDLR rs1799898 at relevant portion shown by SEQ ID NO:15; and selecting a patient having at least one of the specific genotypes for treatment, wherein the treatment comprises administering to the patient at least one compound capable of elevating ketone body concentrations in an amount effective for the treatment of or prevention of reduced cognitive function caused by reduced neuronal metabolism.

In another embodiment, the present invention includes a method of treatment for reduced cognitive function caused by reduced neuronal metabolism. This method may include the steps of selecting a patient having, or at risk of reduced cognitive function caused by reduced neuronal metabolism and determining in the patient the presence of at least one of the specific genotypes including: heterozygosity for C/T for Insulin Degrading Enzyme (IDE) rs2551101 at relevant portion shown by SEQ ID NO:3, absence of homozygosity for C/C of IDE rs2551101 at relevant portion shown by SEQ ID NO:3, heterozygosity for A/C of Apolipoprotein E (APOE) rs405509 at relevant portion shown by SEQ ID NO:21, heterozygosity for G/A of Butyrylcholine esterase (BUCHE) rs1803274 at relevant portion shown by SEQ ID NO:18, homozygosity for adenine of Insulin-like Growth Factor Receptor precursor (IGF1R) rs2229765 at relevant portion shown by SEQ ID NO:6, homozygosity for thymine of Interleukin-1 beta (IL1B) rs1143627 at relevant portion shown by SEQ ID NO:9, homozygosity for cytosine of IL1B rs16944 at relevant portion shown by SEQ ID NO:10, homozygosity for cytosine of Low-density Lipoprotein Receptor (LDLR) rs2738447 at relevant portion shown by SEQ ID NO:24, homozygosity for guanine of LDLR rs7259278 at relevant portion shown by SEQ ID NO:25, and homozygosity for cytosine of LDLR rs1799898 at relevant portion shown by SEQ ID NO:15. The method may further include administering to the patient having at least one of the specific genotypes at least one compound capable of elevating ketone body concentrations in an amount effective for the treatment of or prevention of reduced cognitive function caused by reduced neuronal metabolism.

BRIEF DESCRIPTION OF THE DRAWINGS

FIG. 1 demonstrates interaction between IDE and APOE polymorphisms on Treatment-induced ADAS-Cog change.

DETAILED DESCRIPTION OF THE INVENTION

It is the novel insight of this invention that particular polymorphisms may be useful for selecting patients for treatment for reduced cognitive function caused by reduced neuronal metabolism, wherein the treatment comprises administering to patients at least one compound capable of elevating ketone body concentrations. Particular polymorphisms are associated with "responders," i.e., patient populations in which treatment methods comprising administration of compounds capable of increasing ketone body concentration are associated with efficacy. Also included in the present invention are methods to treat patients having reduced cognitive functions which include testing the patient for particular polymorphisms and selecting a patient for treatment based on the presence of the particular polymorphism.

In one embodiment, the invention comprises a method of selecting a patient having, or at risk of having reduced cognitive function caused by reduced neuronal metabolism, determining in the patient the presence of at least one of the specific genotypes including: heterozygosity for C/T for Insulin Degrading Enzyme (IDE) rs2551101 at relevant portion shown by SEQ ID NO:3, absence of homozygosity for C/C of IDE rs2551101 at relevant portion shown by SEQ ID NO:3, heterozygosity for A/C of Apolipoprotein E (APOE) rs405509 at relevant portion shown by SEQ ID NO:21, heterozygosity for G/A of Butyrylcholine esterase (BUCHE) rs1803274 at relevant portion shown by SEQ ID NO:18, homozygosity for adenine of Insulin-like Growth Factor Receptor precursor (IGF1R) rs2229765 at relevant portion shown by SEQ ID NO:6, homozygosity for thymine of Interleukin-1 beta (IL1B) rs1143627 at relevant portion shown by SEQ ID NO:9, homozygosity for cytosine of IL1B rs16944 at relevant portion shown by SEQ ID NO:10, homozygosity for cytosine of Low-density Lipoprotein Receptor (LDLR) rs2738447 at relevant portion shown by SEQ ID NO:24, homozygosity for guanine of LDLR rs7259278 at relevant portion shown by SEQ ID NO:25, and homozygosity for cytosine of LDLR rs1799898 at relevant portion shown by SEQ ID NO:15; and selecting a patient having at least one of the specific genotypes for treatment, wherein the treatment comprises administering to the patient at least one compound capable of elevating ketone body concentrations in an amount effective for the treatment of or prevention of reduced cognitive function caused by reduced neuronal metabolism.

In another embodiment, the present invention includes a method of treatment for reduced cognitive function caused by reduced neuronal metabolism. This method may include the steps of selecting a patient having, or at risk of reduced cognitive function caused by reduced neuronal metabolism and determining in the patient the presence of at least one of the specific genotypes including: heterozygosity for C/T for Insulin Degrading Enzyme (IDE) rs2551101 at relevant portion shown by SEQ ID NO:3, absence of homozygosity for C/C of IDE rs2551101 at relevant portion shown by SEQ ID NO:3, heterozygosity for A/C of Apolipoprotein E (APOE) rs405509 at relevant portion shown by SEQ ID NO:21, heterozygosity for G/A of Butyrylcholine esterase (BUCHE) rs1803274 at relevant portion shown by SEQ ID NO:18, homozygosity for adenine of Insulin-like Growth Factor Receptor precursor (IGF1R) rs2229765 at relevant portion shown by SEQ ID NO:6, homozygosity for thymine of Interleukin-1 beta (IL1B) rs1143627 at relevant portion shown by SEQ ID NO:9, homozygosity for cytosine of IL1B rs16944 at relevant portion shown by SEQ ID NO:10, homozygosity for cytosine of Low-density Lipoprotein Receptor (LDLR) rs2738447 at relevant portion shown by SEQ ID NO:24, homozygosity for guanine of LDLR rs7259278 at relevant portion shown by SEQ ID NO:25, and homozygosity for cytosine of LDLR rs1799898 at relevant portion shown by SEQ ID NO:15. The method may further include administering to the patient having at least one of the specific genotypes at least one compound capable of elevating ketone body concentrations in an amount effective for the treatment of or prevention of reduced cognitive function caused by reduced neuronal metabolism.

Testing the patient for a specific genotype may be done by methods commonly known in the art. Specifically, based on the particular genotype of interest, it is routine for one of skill to choose appropriate primers. Numerous online tools exist for guidance in primer design, such as, for example, the algorithm Primer3 (v. 0.4.0) which allows choosing appropriate primers for detecting a targeted DNA sequence, available at <frodo.wi.mit.edu>.

Once primers are selected, DNA extraction may be performed by extracting genomic DNA from EDTA anti-coagulated venous blood, which may be accomplished by such art-known methods such as QIA-amp Blood-DNA mini-reagent set (Qiagen) according to the manufacturer's instructions. To detect specific polymorphisms, appropriately designed primer sets may be used to amplify regions containing the polymorphism of interest, using methods known in the art. Genotyping may be ascertained through direct sequencing of PCR products using art known products such as the ABI PRISM BigDye Terminator Cycle Sequencing Ready Reaction Kit and ABI PRISM 377 DNA Sequencer (Applied Biosystems, Foster City, Calif., USA).

In one embodiment, the genotype comprises heterozygosity (C/T) for SNP IDE rs2251101 also known as IDE_7 of Insulin Degrading Enzyme (IDE). In another embodiment, the genotype comprises absence of homozygosity for C/C for SNP rs2251101 also known as IDE_7 of Insulin Degrading Enzyme (IDE). IDE (HGNC Symbol ID). This gene is a member of the human CCDS set: CCDS7421. Ensembl Gene ID: ENSG00000119912. Genomic Location: This gene can be found on Chromosome 10 at location 94,201,421-94,323,813. The start of this gene is located in Contig AL356128.27.1.191935. Description: Insulin-degrading enzyme (EC 3.4.24.56) (Insulysin) (Insulinase) (Insulin protease). Source: Uniprot/SWISSPROT P14735. SEQ ID NO:3 shows a selected portion of this gene identifying polymorphisms of SNP rs2251101.

In another embodiment, the genotype comprises homozygosity for A for rs2229765 of insulin-like growth factor 1 receptor precursor (IGFR-1). IGF1R (HGNC Symbol ID). This gene is a member of the human CCDS set: CCDS10378. Ensembl Gene ID: ENSG00000140443. Genomic Location: This gene can be found on Chromosome 15 at location 97,010,302-97,319,034. The start of this gene is located in Contig AC118658.4.1.168727. Description Insulin-like growth factor 1 receptor precursor (EC 2.7.10.1) (Insulin-like growth factor I receptor) (IGF-I receptor) (CD221 antigen) [Contains: Insulin-like growth factor 1 receptor alpha chain; Insulin-like growth factor 1 receptor beta chain]. Source: Uniprot/SWISSPROT P08069. SEQ ID NO:6 shows a selected portion of this gene identifying polymorphisms of SNP rs2229765.

In another embodiment, the genotype is homozygosity for T at IL1B rs1143627. In another embodiment, the genotype is homozygosity for C at IL1B rs 16944. IL1B(HGNC Symbol ID. This gene is a member of human CCDS set CCDS2102 with Ensembl Gene ID ENSG00000125538. This gene can be found on Chromosome 2 at location 113,303,808-113310,827. The start of this gene is located in Contig AC079753.7.1.154214. Description is Interleukin-1 beta precursor (IL-1 beta) (Catabolin). Source: Uniprot/SWISSPROT P01584. Rs1143627 is a C/T substitution and SEQ ID NO:9 shows a selected portion of this gene identifying placement of this SNP. rs16944 (dbSNP125) is an A/G substitution and SEQ ID NO:10 shows a selected portion of this gene identifying polymorphisms of this SNP.

In another embodiment, the genotype is homozygosity for C at LDLR rs2738447. This gene is a member of the human CCDS set: CCDS12254 with an Ensembl Gene ID ensg00000130164. This gene can be found on Chromosome 19 at location 11,061,155-11,103,838 and the start of this gene is located in Contig AC011485.6.1.128618. Description is Low-density lipoprotein receptor precursor (LDL receptor). Source: Uniprot/SWISSPROT P01130. SEQ ID NO:24 shows a selected portion of this gene identifying polymorphisms of this SNP.

In another embodiment, the genotype is homozygosity for G at LDLR rs7259278. This gene is a member of the human CCDS set: CCDS12254 with an Ensembl Gene ID ensg00000130164. This gene can be found on Chromosome 19 at location 11,061,155-11,103,838 and the start of this gene is located in Contig AC011485.6.1.128618. Description is Low-density lipoprotein receptor precursor (LDL receptor). Source: Uniprot/SWISSPROT P01130. SEQ ID NO:25 shows a selected portion of this gene identifying polymorphisms of this SNP.

In another embodiment, the genotype is homozygosity for C at LDLRrs1799898. LDLR (HGNC Symbol ID). This gene is a member of the human CCDS set: CCDS12254 with an Ensembl Gene ID ensg00000130164. This gene can be found on Chromosome 19 at location 11,061,155-11,103,838 and the start of this gene is located in Contig AC011485.6.1.128618. Description is Low-density lipoprotein receptor precursor (LDL receptor). Source: Uniprot/SWISSPROT P01130. SEQ ID NO:15 shows a selected portion of this gene identifying polymorphisms of SNP rs1799898.

In another embodiment, the genotype is heterozygosity for G/A for Butyrylcholine esterase (BUCHE) K variant rs1803274. BCHE (HGNC Symbol ID). This gene is a member of the human CCDS set CCDS3198. Ensembl Gene ID is ENS00000114200. This gene can be found on Chromosome 3 at location 166,973,387-167,037,944. The start of this gene is located in Contig AC009811.14.1.171083. Cholinesterase precursor (EC 3.1.1.8) (Acylcholine acylhydrolase) (Choline esterase II) (Butyrylcholine esterase) (Pseudocholinesterase). Source: Uniprot/SWISSPROT P06276. SEQ ID NO:18 shows a selected portion of this gene identifying polymorphisms of SNP rs1803274.

In another embodiment, the genotype is heterozygosity for A/C of apolipoprotein E (APOE) promoter variant rs405509. Rs405509 is the −219 variant and has an A/C allele. APOE (HGNC Symbol ID). This gene is a member of the human CCDS set: CCDS12647. Ensemble Gene ID is ENSG00000130203. This gene can be found on Chromosome 19 at location 50,100,879-50,104,489. The start of this gene is located in Contig AC011481.4.1.107567. Apolipoprotein E precursor (Apo-E). Source: Uniprot/SWISSPROT P02649. SEQ ID NO:21 shows a selected portion of this gene identifying polymorphisms of SNP rs405509.

As used herein, reduced neuronal metabolism refers to all possible mechanisms that could lead to a reduction in neuronal metabolism. Such mechanisms include, but are not limited to mitochondrial dysfunction, free radical attack, generation of reactive oxygen species (ROS), ROS-induced neuronal apoptosis, defective glucose transport or glycolysis, imbalance in membrane ionic potential, dysfunction in calcium flux, and the like. In another embodiment, the patient has or is at risk of developing disease-related reduced cognitive function caused by reduced neuronal metabolism, for example, reduced cognitive function associated with Alzheimer's Disease (AD), Parkinson's Disease, Friedreich's Ataxia (FRDA), GLUT1-deficient Epilepsy, Leprechaunism, and Rabson-Mendenhall Syndrome, Coronary Arterial Bypass Graft (CABG) dementia, anesthesia-induced memory loss, Huntington's Disease, and many others.

According to the present invention, high blood ketone levels will provide an energy source for brain cells that have compromised glucose metabolism, leading to improved performance in cognitive function. As used herein, "patient" refers to any mammal, including humans that may benefit from treatment of disease and conditions resulting from reduced neuronal metabolism.

In one embodiment, a compound capable of elevating a ketone body concentrations in the body of a mammal include "medium chain triglycerides" or "MCT", referring to any glycerol molecule ester-linked to three fatty acid molecules, each fatty acid molecule having a carbon chain of 5-12 carbons. MCT may be represented by the following general formula:

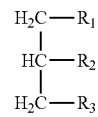

where R1, R2 and R3 are fatty acids having 5-12 carbons in the carbon backbone esterified to the a glycerol backbone. The structured lipids of this invention may be prepared by any process known in the art, such as direct esterification, rearrangement, fractionation, transesterification, or the like. For example, the lipids may be prepared by the rearrangement of a vegetable oil such as coconut oil. The length and distribution of the chain length may vary depending on the source oil. For example, MCT containing 1-10% C6, 30-60% C8, 30-60% CIO, 1-10% CIO are commonly derived from palm and coconut oils. MCT containing greater than about 95% C8 at R1, R2 and R3 can be made by semi-synthetic esterification of octanoic acid to glycerin. Such MCT behave similarly and are encompassed within the term MCT as used herein.

MCT are comprised of fatty acids with chain length between 5-12 carbons and have been researched extensively. MCT are metabolized differently from the more common Long Chain Triglycerides (LCT). In particular, when compared to LCT, MCT are more readily digested to release medium chain fatty acids (MCFA) which exhibit increased rates of portal absorption, and undergo obligate oxidation. MCFA have melting points much lower than long chain fatty acids (LCFA), and therefore the MCFA and corresponding MCT are liquid at room temperature. MCFA are smaller and more ionized at physiological pH compared to LCFA, and hence MCFA are much more soluble in aqueous solutions. The small size and decreased hydrophobicity of MCT increases the rate of digestion and absorption relative to LCT.

When ingested, MCT are first processed by lipases, which cleave the fatty acid chains from the glycerol backbone. Some lipases in the pre-duodenum preferentially hydrolyze MCT over LCT and the released MCFA are then partly absorbed directly by the stomach mucosa. Those MCFA which are not absorbed in the stomach are absorbed directly into the portal vein and not packaged into lipoproteins. LCFA derived from normal dietary fat are re-esterified into LCT and packaged into chylomicrons for transport in the lymph. This greatly slows the metabolism of LCT relative to MCT. Since blood transports much more rapidly than lymph, MCFA quickly arrive at the liver.

In the liver MCFA undergo obligate oxidation. In the fed state LCFA undergo little oxidation in the liver, due mainly to the inhibitory effects of malonyl-CoA. When conditions favor fat storage, malonyl-CoA is produced as an intermediate in lipogenesis. Malonyl-CoA allosterically inhibits carnitine palmitoyltransferase I, and thereby inhibits LCFA transport into the mitochondria. This feedback mechanism prevents futile cycles of lipolysis and lipogenesis. MCFA are, to a large extent, immune to the regulations that control the oxidation of LCFA. MCFA enter the mitochondria without the use of carnitine palmitoyltransferase I, therefore MCFA by-pass this regulatory step and are oxidized regardless of the metabolic state of the organism. Importantly, since MCFA enter the liver rapidly and are quickly oxidized, large amounts of ketone bodies are readily produced from MCFA and a large oral dose of MCT (roughly 20 mL) will result in sustained hyperketonemia. It is the novel insight of the inventor that MCT may be administered outside of the context of a ketogenic diet. Therefore, in the present invention carbohydrates may be consumed at the same time as MCT.

"Effective amount" refers to an amount of a compound, material, or composition, as described herein that is effective to achieve a particular biological result. Effectiveness for treatment of the aforementioned conditions may be assessed by improved results from at least one neuropsychological test. These neuropsychological tests are known in the art and include Clinical Global Impression of Change (CGIC), Rey Auditory Verbal Learning Test (RAVLT), First-Last Names Association Test (FLN), Telephone Dialing Test (TDT), Memory Assessment Clinics Self-Rating Scale (MAC-S), Symbol Digit Coding (SDC), SDC Delayed Recall Task (DRT), Divided Attention Test (DAT), Visual Sequence Comparison (VSC), DAT Dual Task (DAT Dual), Mini-Mental State Examination (MMSE), and Geriatric Depression Scale (GDS), among others.

The term "cognitive function" refers to the special, normal, or proper physiologic activity of the brain, including, without limitation, at least one of the following: mental stability, memory/recall abilities, problem solving abilities, reasoning abilities, thinking abilities, judging abilities, capacity for learning, perception, intuition, attention, and awareness. "Enhanced cognitive function" or "improved cognitive function" refers to any improvement in the special, normal, or proper physiologic activity of the brain, including, without limitation, at least one of the following: mental stability, memory/recall abilities, problem solving abilities, reasoning abilities, thinking abilities, judging abilities, capacity for learning, perception, intuition, attention, and awareness, as measured by any means suitable in the art. "Reduced cognitive function" or "impaired cognitive function" refers to any decline in the special, normal, or proper physiologic activity of the brain.

Administration can be on an as-needed or as-desired basis, for example, once-monthly, once-weekly, daily, or more than once daily. Similarly, administration can be every other day, week, or month, every third day, week, or month, every fourth day, week, or month, and the like. Administration can be multiple times per day. When utilized as a supplement to ordinary dietetic requirements, the composition may be administered directly to the patient or otherwise contacted with or admixed with daily feed or food.

Administration can also be carried out on a regular basis, for example, as part of a treatment regimen in the patient. A treatment regimen may comprise causing the regular ingestion by the patient of an inventive composition in an amount effective to enhance cognitive function, memory, and behavior in the patient. Regular ingestion can be once a day, or two, three, four, or more times per day, on a daily or weekly basis. Similarly, regular administration can be every other day or week, every third day or week, every fourth day or week, every fifth day or week, or every sixth day or week, and in such a regimen, administration can be multiple times per day. The goal of regular administration is to provide the patient with optimal dose of an inventive composition, as exemplified herein.

The compositions provided herein are, in one embodiment, intended for "long term" consumption, sometimes referred to herein as for 'extended' periods. "Long term" administration as used herein generally refers to periods in excess of one month. Periods of longer than two, three, or four months comprise one embodiment of the instant invention. Also included are embodiments comprising more extended periods that include longer than 5, 6, 7, 8, 9, or 10 months. Periods in excess of 11 months or 1 year are also included. Longer terms use extending over 1, 2, 3 or more years are also contemplated herein. "Regular basis" as used herein refers to at least weekly, dosing with or consumption of the compositions. More frequent dosing or consumption, such as twice or thrice weekly are included. Also included are regimens that comprise at least once daily consumption. The skilled artisan will appreciate that the blood level of ketone bodies, or a specific ketone body, achieved may be a valuable measure of dosing frequency. Any frequency, regardless of whether expressly exemplified herein, that allows maintenance of a blood level of the measured compound within acceptable ranges can be considered useful herein. The skilled artisan will appreciate that dosing frequency will be a function of the composition that is being consumed or administered, and some compositions may require more or less frequent administration to maintain a desired blood level of the measured compound (e.g., a ketone body).

In one embodiment, the method comprises the use of MCT wherein R1, R2, and R3 are fatty acids containing a six-carbon backbone (tri-C6:0). Tri-C6:0 MCT are absorbed very rapidly by the gastrointestinal tract in a number of animal model systems. The high rate of absorption results in rapid perfusion of the liver, and a potent ketogenic response. In another embodiment, the method comprises the use of MCT wherein R1, R2, and R3 are fatty acids containing an eight-carbon backbone (tri-C8:0). In another embodiment, the method comprises the use of MCT wherein R1, R2, and R3 are fatty acids containing a ten-carbon backbone (tri-C10:0). In another embodiment, the method comprises the use of MCT wherein R1, R2, and R3 are a mixture of C8:0 and C 10:0 fatty acids. In another embodiment, the method comprises the use of MCT wherein R1, R2 and R3 are a mixture of C6:0, C8:0, C10:0, and C12:0 fatty acids. In another embodiment, greater than 95% of R1, R2 and R3 carbon chains of the MCT are 8 carbons in length. In yet another embodiment, the R1, R2, and R3 carbon chains are 6-carbon or 10-carbon chains. In another embodiment, 50% of the R1, R2 and R3 carbon chains of the MCT are 8 carbons in length and about 50% of the R1, R2 and R3 carbon chains of the MCT are about 10 carbons in length. Additionally, utilization of MCT can be increased by emulsification. Emulsification of lipids increases the surface area for action by lipases, resulting in more rapid hydrolysis and release of MCFA. Methods for emulsification of these triglycerides are well known to those skilled in the art.

In one embodiment, the method comprises the use of MCFA of 6, 8, 10 and 12 carbon chain length or mixtures of the above.

Therapeutically effective amounts of the therapeutic agents can be any amount or dose sufficient to bring about the desired effect and depend, in part, on the severity and stage of the condition, the size and condition of the patient, as well as other factors readily known to those skilled in the art. The dosages can be given as a single dose, or as several doses, for example, divided over the course of several weeks, as discussed elsewhere herein.

In one embodiment, the ketogenic compounds are administered orally. In another embodiment, the ketogenic compounds are administered intravenously. Oral administration of MCT and other ketogenic compound preparations of intravenous MCT and other ketogenic compound solutions are well known to those skilled in the art.

In one embodiment, oral and/or intravenous administration of a composition comprising at least one compound capable of elevating ketone body concentrations, such as, for example, MCT or MCFA, result in hyperketonemia. Hyperketonemia, in one embodiment, results in ketone bodies being utilized for energy in the brain even in the presence of glucose. Additionally, hyperketonemia results in a substantial (39%) increase in cerebral blood flow (Hasselbalch, S. G., et al., Changes in cerebral blood flow and carbohydrate metabolism during acute hyperketonemia, *Am J Physiol*, 1996, 270: E746-51). Hyperketonemia has been reported to reduce cognitive dysfunction associated with systemic hypoglycemia in normal humans (Veneman, T., et al., Effect of hyperketonemia and hyperlacticacidemia on symptoms, cognitive dysfunction, and counterregulatory hormone responses during hypoglycemia in normal humans, *Diabetes*, 1994, 43:1311-7). Please note that systemic hypoglycemia is distinct from the local defects in glucose metabolism that occur in any disease- or age-associated cognitive decline, such as AD, AAMI, and the like.

In all embodiments, the invention provides the subject compositions comprising at least one compound that is capable of elevating ketone body concentrations. Such compounds are also collectively referred to as ketone body precursor compounds or ketogenic compounds. Such compounds include compounds such as, for example, MCT, MCFA, and prodrugs, metabolic precursors, and so on, of ketone bodies. For example, in one embodiment, the compound capable of elevating ketone body concentrations in the body include one or more prodrugs, which can be metabolically converted to the subject compounds by the recipient host. As used herein, a prodrug is a compound that exhibits pharmacological activity after undergoing a chemical transformation in the body. A prodrug can also be referred to as a metabolic precursor if the conversion of the prodrug directly results in the formation of a ketone body. MCT and MCFA must be first oxidized to acetyl-CoA, then undergo several steps before being synthesized into ketone bodies. The class of ketone body precursor compounds include, the compounds described hereinbelow. The ketone body precursor compounds, in one embodiment, are administered in a dosage required to increase blood ketone bodies to a level required to treat and/or prevent the occurrence of any disease- or age-associated cognitive decline, such as AD, AAMI, and the like. Appropriate dosages of all of these compounds can be determined by one of skill in the art.

A wide variety of prodrug formulations are known in the art. For example, prodrug bonds may be hydrolyzable, such as esters or anhydrides, or enzymatically biodegradable, such as amides.

Ketone body precursor compounds e.g., compounds capable of elevating ketone body concentrations, appropriate for use with the present invention includes any compounds that are capable of directly elevating ketone body concentrations in the body of a mammal, e.g., a patient, and may be determined by one of skill in the art. These compounds can mimic the effect of increasing oxidation of fatty acids and include but are not limited to the ketone bodies, D-beta-hydroxybutyrate and acetoacetate, and metabolic precursors of these. The term metabolic precursor, used in this embodiment, can refer to compounds that comprise 1,3 butane diol, acetoacetyl or D-beta-hydroxybutyrate moieties such as acetoacetyl-1-1,3-butane diol, acetoacetyl-D-beta-hydroxybutyrate, and acetoacetylglycerol. Esters of any such compound with monohydric, dihydric or trihydric alcohols are also included in yet another embodiment. Metabolic precursors also include polyesters of D-beta-hydroxybutyrate, and acetoacetate esters of D-beta-hydroxybutyrate. Polyesters of D-beta-hydroxybutyrate include oligomers of this polymer designed to be readily digestible and/or metabolized by humans or mammals. These preferably are of 2 to 100 repeats long, typically 2 to 20 repeats long, and most conveniently from 3 to 10 repeats long. Examples of poly D-beta-hydroxybutyrate or terminally oxidized poly-D-beta-hydroxybutyrate esters useable as ketone body precursors are given below:

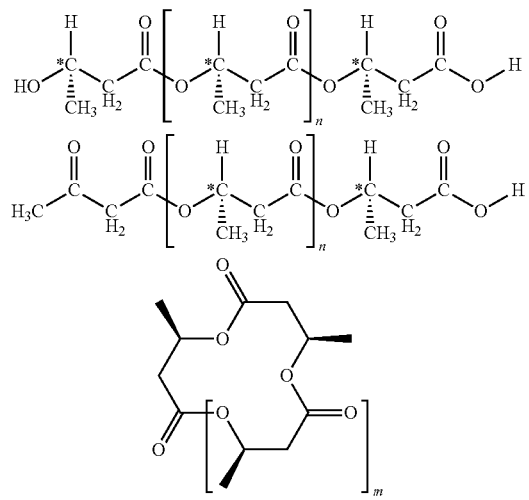

In each case, n is selected such that the polymer or oligomer is readily metabolized on administration to a human or mammal body to provide elevated ketone body levels in blood. Values of n are integers of 0 to 1,000, more preferably 0 to 200, still more preferably 1 to 50, most preferably 1 to 20, particularly conveniently being from 3 to 5. In each case m is an integer of 1 or more, a complex thereof with one or more cations or a salt thereof for use in therapy or nutrition. Examples of cations and typical physiological salts are described herein, and additionally include sodium, potassium, magnesium, calcium, each balanced by a physiological counter-ion forming a salt complex, L-lysine, L-arginine, methyl glucamine, and others known to those skilled in the art.

Also included in the definition of a ketone body precursor compound are several other ketone body precursor compounds useful for treating reduced neuronal metabolism; including esters of polyhydric alcohols, 3-hydroxyacid esters and glycerol esters, as described more fully hereinbelow. As used herein, "derivative" refers to a compound or portion of a compound that is derived from or is theoretically derivable from a parent compound; The term "hydroxyl group" is represented by the formula —OH; the term "alkoxy group" is represented by the formula —OR, where R can be an alkyl group, including a lower alkyl group, optionally substituted with an alkenyl, alkynyl, aryl, aralkyl, cycloalkyl, halogenated alkyl, or heterocycloalkyl group, as defined below; the term "ester" is represented by the formula —OC(O)R, where R can be an alkyl, alkenyl, alkynyl, aryl, aralkyl, cycloalkyl, halogenated alkyl, or heterocycloalkyl group, as defined below; the term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms; the term "alkenyl group" is defined as a hydrocarbon group of 2 to 24 carbon atoms and structural formula containing at least one carbon-carbon double bond; the term "alkynyl group" is defined as a hydrocarbon group of 2 to 24 carbon atoms and a structural formula containing at least one carbon-carbon triple bond; the term "halogenated alkyl group" is defined as an alkyl group as defined above with one or more hydrogen atoms present on these groups substituted with a halogen (F, Cl, Br, I); the term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous; the term "aliphatic group" is defined as including alkyl, alkenyl, alkynyl, halogenated alkyl and cycloalkyl groups as defined above. A "lower aliphatic group" is an aliphatic group that contains from 1 to 10 carbon atoms; the term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted; the term "aralkyl" is defined as an aryl group having an alkyl group, as defined above, attached to the aryl group. An example of an aralkyl group is a benzyl group; "esterification" refers to the reaction of an alcohol with a carboxylic acid or a carboxylic acid derivative to give an ester; "transesterification" refers to the reaction of an ester with an alcohol to form a new ester compound. The term "3-hydroxybutyrate" is used interchangeably with the term "3-hydroxybutyric acid."

In one embodiment, a compound capable of elevating ketone body concentrations includes compounds according to formula:

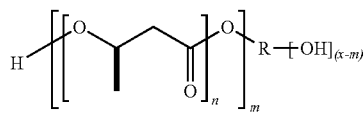

wherein R is a polyhydric alcohol residue; n, m and x represent integers; and m is less than or equal to x.

Physiologically compatible alcohols suitable for forming esters with (R)-3-hydroxybutyrate and derivatives thereof include monohydric and polyhydric alcohols. Esters of polyhydric alcohols deliver a higher density of (R)-3-hydroxybutyrate equivalents per equivalent of (R)-3-hydroxybutyrate derivative using shorter (R)-3-hydroxybutyrate oligomers. Shorter oligomers generally are more readily hydrolyzed to give elevated concentrations of (R)-3-hydroxybutyrate in blood. Examples of polyhydric alcohols suitable for preparing such esters include carbohydrates and carbohydrate derivatives, such as carbohydrate alcohols, examples of carbohydrates include, without limitation, altrose, arabinose, dextrose, erythrose, fructose, galactose, glucose, gulose, idose, lactose, lyxose, mannose, ribose, sucrose, talose, threose, xylose and the like. Additional examples of carbohydrates useful for preparing (R)-3-hydroxybutyrate derivatives include amino derivatives, such as galactosamine, glucosamine and mannosamine, including N-acetyl derivatives, such as N-acetylglucosamine and the like. Examples of carbohydrates also include carbohydrate derivatives, such as alkyl glycosides. Examples of carbohydrate alcohols include, without limitation, glycerol, mannitol, ribitol, sorbitol, threitol, xylitol and the like. The enantiomers of the above-listed carbohydrates and carbohydrate alcohols also can be used to prepare (R)-3-hydroxybutyrate derivatives according to the above formula.

Embodiments include compounds where n is from 1 to about 100; wherein x is from 1 to about 20; wherein m is from 1 to about 20. One embodiment includes a compound wherein R is (R)-1,3-butanediol.

In another embodiment, compounds capable of elevating ketone body concentrations include compounds of the formula

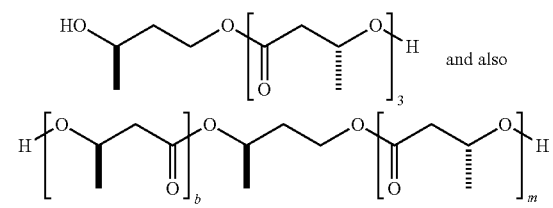

where n and m independently are integers from 1 to about 100. In some embodiments, n and m are the same; n and m are different; and wherein n and m are 3.

In addition, compounds capable of elevating ketone body concentrations include ester compounds of R-3-hydroxybutyrate according to the formula

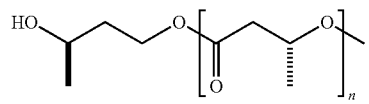

wherein n is an integer from 1 to about 100. In one embodiment, n is 3.

Other compounds capable of elevating ketone body levels include 3-hydroxyacids. The compositions include 3-hydroxyacids, linear or cyclic oligomers thereof, esters of the 3-hydroxyacids or oligomers, derivatives of 3-hydroxyacids, and combinations thereof. In one embodiment, the compositions include the cyclic macrolide of R-3-hydroxyacids containing 3, 4, or 5 monomeric subunits. 3-hydroxyacids include 3-hydroxybutyric acid, 3-hydroxyvaleric acid, 3-hydroxyhexanoic acid and 3-hydroxyheptanoic acid. In some embodiments, the length of the oligomer must be such that the derivative has a suitable digestion rate for sustained release of monomer. In another embodiment, the cyclic trimer (triolide) is used in a combination with other cyclic oligolides or linear esters and/or mixtures of both.

The general formula for 3-hydroxyacids is:

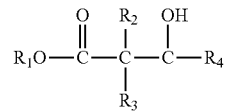

wherein $R_1$ is selected from hydrogen, methyl, alkyl, alkenyl, aryl, arylalkyl, heteroalkyl, heteroaryl, thiol, disulfide, ether, thiolether, amine, amide, halogen. $R_2$ and $R_3$ are independently selected from hydrogen, methyl, alkyl, alkenyl, aryl, arylalkyl, heteroalkyl, heteroaryl, thiol, disulfide, ether, thiolether, amine, amide, halogen, hydroxy, ester, nitrogen-substituted radicals, and/or oxygen-substituted radicals. $R_4$ is selected from hydrogen, alkyl, alkenyl, aryl, arylalkyl, heteroalkyl, heteroaryl, thiol, disulfide, ether, thiolether, amine, amide, halogen, hydroxy, ester, nitrogen-substituted radicals, and/or oxygen-substituted radicals. Further, when $R_4$ is not hydrogen or a halogen, $R_3$ can be a direct bond to $R_4$ and $R_4$ can be methyl.

Other compounds capable of elevating ketone body levels include glycerol esters, namely, not readily water-soluble glycerides of at least one keto or hydroxy acid, having the formula

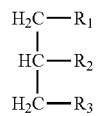

wherein two or three of the groups $R_1$, $R_2$ and $R_3$ independently of each other, are one or more of the groups acetoacetate, alpha-ketopropionate, beta-hydroxybutyrate and alpha-hydroxypropionate, and when only two of the groups $R_1$, $R_2$ and $R_3$ are any of said groups, the third of them is a hydroxy group or a residue of a saturated or unsaturated fatty acid containing 2 to 24 carbon atoms. Other glycerol esters are envisioned, particularly not readily water-soluble glycerides of at least one keto or hydroxy acid, having the formula

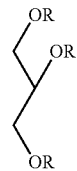

wherein one R group is hydrogen, and two R groups are (—$COCH_2$, $COCH_3$). Additionally, wherein each R is the same or different and is hydrogen, or (—$COCH_2$, $COCH_3$), provided that at least one R is not hydrogen and wherein R' is a linear acid ester of even carbon number from 2 to 20 carbons.

This invention also provides the inventive compositions in one embodiment in administratively convenient formulations including dosage units incorporated into a variety of containers. Dosages of the inventive compositions, such as, for example, those comprising MCT, may be administered in an effective in an effective amount to increase the cognitive ability of patients afflicted with diseases of reduced neuronal metabolism, such as in patients with any disease- or age-associated cognitive decline, such as, AD, AAMI, and the like.

In one embodiment, the inventive compositions result in elevating ketone concentrations in the body, and in this embodiment, the compositions are administered in an amount that is effective to induce hyperketonemia. In one embodiment, hyperketonemia results in ketone bodies being utilized for energy in the brain.

In one embodiment, the composition increases the circulating concentration of at least one type of ketone body in the mammal or patient. In one embodiment, the circulating ketone body is D-beta-hydroxybutyrate. The amount of circulating ketone body can be measured at a number of times post administration, and in one embodiment, is measured at a time predicted to be near the peak concentration in the blood, but can also be measured before or after the predicted peak blood concentration level. Measured amounts at these off-peak times are then optionally adjusted to reflect the predicted level at the predicted peak time. In one embodiment, the predicted peak time is at about two hours. Peak circulating blood level and timing can vary depending on factors known to those of skill in the art, including individual digestive rates, co-ingestion or pre- or post-ingestion of foods, drinks, etc., as known to one of skill in the art. In one embodiment, the peak blood level reached of D-beta-hydroxybutyrate is between about 0.05 millimolar (mM) to about 50 mM. Another way to determine whether blood levels of D-beta-hydroxybutyrate are raised to about 0.05 to about 50 mM is by measurement of D-beta-hydroxybutyrate urinary excretion a range in the range of about 5 mg/dL to about 160 mg/dL. In other embodiments, the peak blood level is raised to about 0.1 to about 50 mM, from about 0.1 to about 20 mM, from about 0.1 to about 10 mM, to about 0.1 to about 5 mM, more preferably raised to about 0.15 to about 2 mM, from about 0.15 to about 0.3 mM, and from about 0.2 to about 5 mM, although variations will necessarily occur depending on the formulation and host, for example, as discussed above. In other embodiments, the peak blood level reached of D-beta-hydroxybutyrate will be at least about 0.05 mM, at least about 0.1 mM, at least about 0.15 mM, at least about 0.2 mM, at least about 0.5 mM, at least about 1 mM, at least about 1.5 mM, at least about 2 mM, at least about 2.5 mM, at least about 3 mM, at least about 4 mM, at least about 5 mM, at least about 10 mM, at least about 15 mM, at least about 20 mM, at least about 30 mM, at least about 40 mM, and at least about 50 mM.

Effective amount of dosages of compounds for the inventive compositions, i.e., compounds capable of elevating ketone body concentrations in an amount effective for the treatment of or prevention of loss of cognitive function caused by reduced neuronal metabolism will be apparent to those skilled in the art. As discussed herein above, such effective amounts can be determined in light of disclosed blood ketone levels. Where the compound capable of elevating ketone body concentrations is MCT, the MCT dose, in one embodiment, is in the range of about 0.05 g/kg/day to about 10 g/kg/day of MCT. In other embodiments, the dose will be in the range of about 0.25 g/kg/day to about 5 g/kg/day of MCT. In other embodiments, the dose will be in the range of about 0.5 g/kg/day to about 2 g/kg/day of MCT. In other embodiments, the dose will be in the range of about 0.1 g/kg/day to about 2 g/kg/day. In other embodiments, the dose of MCT is at least about 0.05 g/kg/day, at least about 0.1 g/kg/day, at least about 0.15 g/kg/day, at least about 0.2 g/kg/day, at least about 0.5 g/kg/day, at least about 1 g/kg/day, at least about 1.5 g/kg/day, at least about 2 g/kg/day, at least about 2.5 g/kg/day, at least about 3 g/kg/day, at least about 4 g/kg/day, at least about 5 g/kg/day, at least about 10 g/kg/day, at least about 15 g/kg/day, at least about 20 g/kg/day, at least about 30 g/kg/day, at least about 40 g/kg/day, and at least about 50 g/kg/day.

Convenient unit dosage containers and/or formulations include tablets, capsules, lozenges, troches, hard candies, nutritional bars, nutritional drinks, metered sprays, creams, and suppositories, among others. The compositions may be combined with a pharmaceutically acceptable excipient such as gelatin, oil(s), and/or other pharmaceutically active agent (s). For example, the compositions may be advantageously combined and/or used in combination with other therapeutic or prophylactic agents, different from the subject compounds. In many instances, administration in conjunction with the subject compositions enhances the efficacy of such agents. For example, the compounds may be advantageously used in conjunction with antioxidants, compounds that enhance the efficiency of glucose utilization, and mixtures thereof.

In one embodiment, the subject is intravenously infused with ketogenic compounds such as MCT, MCFA, directly, to a level required to treat and prevent the occurrence of diseases of reduced neuronal metabolism. Preparation of intravenous lipids and ketone body solutions are well known to those skilled in the art.

In one embodiment, the invention provides a formulation comprising a mixture of MCT and carnitine to provide elevated blood ketone levels. The nature of such formulations will depend on the duration and route of administration. Such formulations can be in the range of 0.05 g/kg/day to 10 g/kg/day of MCT and 0.05 mg/kg/day to 10 mg/kg/day of carnitine or its derivatives. In one embodiment, an MCT dose can be in the range of 0.05 g/kg/day to 10 g/kg/day of MCT. The dose can be in the range of 0.25 g/kg/day to 5 g/kg/day of MCT. The dose can also be in the range of 0.5 g/kg/day to 2 g/kg/day of MCT. In some embodiments, a carnitine or carnitine derivative dose can be in the range of 0.05 mg/kg/day to 10 mg/kg/day. The carnitine or carnitine derivative dose can be in the range of 0.1 mg/kg/day to 5 mg/kg/day. The carnitine or carnitine derivative dose can also be in the range of 0.5 mg/kg/day to 1 mg/kg/day. Variations will necessarily occur depending on the formulation and/or host, for example.

In one embodiment, a formulation comprises a range of about 1 to about 500 g of emulsified MCT combined with about 1 to about 2000 mg of carnitine. Amounts of MCT can be at least about 1 g, at least about 10 g, at least about 50 g, at least about 100 g, at least about 150 g, at least about 200 g, at least about 250 g, at least about 300 g, at least about 400 g. Amounts of carnitine can be at least about 1 g, at least about 50 g, at least about 100 g, at least about 250 g, at least about 500 g, at least about 1000 g, at least about 1250 g, at least about 1500 g. Another formulation comprises 50 g MCT (95% triC8:0) emulsified with 50 g of mono- and di-glycerides combined with 500 mg of L-carnitine. Such a formulation is well tolerated and generally induces hyperketonemia for 3-4 hours in human subjects.

The daily dose of MCT can be also be measured in terms of grams of MCT per kg of body weight (BW) of the mammal. The daily dose of MCT can range from about 0.01 g/kg to about 10.0 g/kg BW of the mammal. Preferably, the daily dose of MCT is from about 0.1 g/kg to about 5 g/kg BW of the mammal. More preferably, the daily dose of MCT is from about 0.2 g/kg to about 3 g/kg of the mammal. Still more preferably, the daily dose of MCT is from about 0.5 g/kg to about 2 g/kg of the mammal.

In some embodiments, the inventive compounds may be co administered with carbohydrate, or be co-formulated with carbohydrate. Carbohydrate can include more than one type of carbohydrate. Appropriate carbohydrates are known in the art, and include simple sugars, such as glucose, fructose, sucrose, and the like, from conventional sources such as corn syrup, sugar beet, and the like. If co-formulated, the amount of carbohydrate to use can include at least about 0.1 g, at least about 1 g, at least about 10 g, at least about 50 g, at least about 100 g, at least about 150 g, at least about 200 g, at least about 250 g, at least about 300 g, at least about 400 g. Amounts of carnitine can be at least about 1 g, at least about 50 g, at least about 100 g. The compositions can comprise from about 15% to about 40% carbohydrate, on a dry weight basis. Sources of such carbohydrates include grains or cereals such as rice, corn, sorghum, alfalfa, barley, soybeans, canola, oats, wheat, or mixtures thereof. The compositions also optionally comprise other components that comprise carbohydrates such as dried whey and other dairy products or by-products.

In another embodiment, the methods of the present invention further comprise determination of the patients' genotype or particular alleles. In one embodiment, the patient's alleles of the apolipoprotein E gene are determined. It has been found that non-E4 carriers performed better than those with the E4 allele when elevated ketone body levels were induced with MCT. Also, those with the E4 allele had higher fasting ketone body levels and the levels continued to rise at the two hour time interval. Therefore, E4 carriers may require higher ketone levels or agents that increase the ability to use the ketone bodies that are present.

In another embodiment, the compositions comprising compounds capable of increasing ketone body concentrations are food products formulated specifically for human consumption. These will include foods and nutrients intended to supply necessary dietary requirements of a human being as well as other human dietary supplements. In a one embodiment, the food products formulated for human consumption are complete and nutritionally balanced while in others they are intended as nutritional supplements to be used in connection with a well-balanced or formulated diet.

In another embodiment, the composition is a food supplement, such as drinking water, beverage, liquid concentrate, gel, yogurt, powder, granule, paste, suspension, chew, morsel, treat, snack, pellet, pill, capsule, tablet, or any other delivery form. The nutritional supplements can be specially formulated for consumption by a particular species or even an individual mammal, such as companion mammal, or a human. In one embodiment, the nutritional supplement can comprise a relatively concentrated dose of MCT such that the supplement can be administered to the mammal in small amounts, or can be diluted before administration to a mammal. In some embodiments, the nutritional supplement or other MCT-containing composition may require admixing with water or the like prior to administration to the mammal, for example to adjust the dose, to make it more palatable, or to allow for more frequent administration in smaller doses.

Sources of the MCT include any suitable source, semi-synthetic, synthetic or natural. Examples of natural sources of MCT include plant sources such as coconuts and coconut oil, palm kernels and palm kernel oils, and animal sources such as milk from any of a variety of species, e.g., goats.

EXAMPLES

The following examples are provided for illustrative purposes only and are not intended to limit the scope of the invention.

Example 1

Pharmacogenomics in a Ketone Body Based Treatment of Alzheimer's Disease

One promising treatment for Alzheimer's disease is the induction of ketosis. Study KET-04-001 examined the pharmacogenomic effects of several genetic markers in a group of mild to moderate AD patients treated with a ketogenic agent. The test compound was AC-1202. AC-1202 is a formulation of medium chain triglycerides (MCT) designed to safely elevate serum ketone bodies even in the presence of carbohydrate in the diet. MCT were chosen for this study due to their excellent safety profile and long historical use in lipid malabsorption disorders and ketogenic diets. Due to the unique physical properties of AC-1202, it is metabolized differently from the more common long chain triglycerides (LCT). If sufficiently large amounts of AC-1202 are consumed a mild state of ketosis can be induced.

Subjects

Two hundred fifty-three participants with a diagnosis of probable AD were screened. The study recruited outpatients with a diagnosis of probable AD of mild to moderate severity according to NINCDS-ADRDA and DSM IV criteria, with a MMSE score of between 14 and 24 (inclusive) at Screen. A CT or MRI within 24 months prior to Screen had to show no signs of tumor, structural abnormality, or degenerative disease. Subjects were required to have a Modified Hachinski Ischemia Scale score 54. Subjects and their caregivers provided informed consent, which included an optional provision for genotyping. At their discretion, participants could consent to be tested for APOE, and/or additional DNA markers. Genetic information was not shared with site personnel or study participants.

Key exclusion criteria at Screen included: major depression as determined by a Cornell Scale for Depression in Dementia score of clinically significant hypothyroidism as determined by thyroid function assessment, clinically significant B12 deficiency within 12 months prior to Baseline, clinically significant renal disease or insufficiency, clinically significant hepatic disease or insufficiency, and any type of diabetes.

Subjects receiving currently approved AD medications were eligible for enrollment in the study provided that they had been maintained on stable dosing for at least 3 months prior to Screen and were required to remain on stable dosing throughout the duration of the study.

Study Design

Subjects were randomized in a 1:1 ratio to receive either AC-1202 or matching Placebo for 90 days. A permutated block randomization code with a block size of 4 was used. Subjects were issued study kits labeled with a unique site and subject number. The participants, those administering the interventions, and those assessing the outcomes were blinded to group assignment. Subjects who prematurely discontinued the study were replaced and assigned to investigational product by an independent un-blinded medical monitor in such a manner as to obtain approximately 50 subjects within each treatment group.

Investigational product was formulated as an emulsified spray dried powder consisting of 33% AC-1202 (NeoBee 895, Stepan Chemical Company), 64% gum Acacia (Instagum, CNI) and 2.6% syloid (244FP, Grace Davison). Placebo was isocaloric to the active formulation and consisted of a mixture of 51% gum acacia, 37% dextrose, 10% safflower oil and 2% syloid (prepared by The Chemins Company). Investigational product was given as a powder packaged in 30 gram sachets containing either active (equivalent to 10 grams of AC-1202) or matching Placebo.

The contents of the sachets were to be mixed in one 8 oz. glass of a liquid such as water, milk, or juice prior to consumption. These instructions were later amended to recommend reconstitution with a meal replacement drink, Ensure (Abbott Laboratories), to improve product tolerability. For the first seven days of the study, subjects received one 30 gm sachet daily. On Day 8, each subject was asked to increase the dose to two 30 gm sachets daily, and continue on that dose through Day 90. Daily doses were administered during breakfast, except on clinic visit days when the participants were asked to eat breakfast prior to their scheduled visit.

Safety evaluations included physical examinations, vital sign measurements, routine serum chemistry and hematology tests, and electrocardiograms performed at Screen and Day 104. Treatment emergent adverse events and any changes in concomitant medication administration were recorded at all clinic visits.

Assays β-hydroxybutyrate Concentration Levels

Pre- and post-dosing serum samples were collected and analyzed by Allied Research International (formerly SFBC) of Miami, Fla. using the BHB Liquicolor® diagnostic kit supplied by Stanbio Laboratories (Boenre, Tex.). The normal range (12-hour fasting) is 0.02 mM to 0.27 mM.

Statistical Analysis

An intention-to-treat (ITT) analysis was used as the primary analysis of efficacy, where all subjects who were randomized, received study medication, and who completed at least one follow-up visit were included. All missing efficacy data were imputed using the last observation carried forward (LOCF) method. The primary end points established a priori were change from baseline in ADAS-Cog and the ADCS-CGIC global scores at Day 90. Secondary outcome measures included the MMSE, and interactions associated with APOE genotype and BHB concentration levels.

An overall two-way ANCOVA was used to evaluate the treatment effect, along with genotype effects and treatment by genotype interactions for Cmax serum BHB levels at Day 90. The ANCOVA model included independent factors for treatment, genotype, and treatment by genotype interactions. A variable for baseline serum BHB level was included as a covariate. Correlations between the Cmax serum BHB level on Day 90 and the change from baseline total score was determined by Pearson correlation statistics.

Genotyping

Several genetic markers were chosen for their ability to influence the effectiveness of a ketone body based therapy in Alzheimer's disease in Study KET-04-001. Participants in Study KET-04-001 who consented to additional genetic analysis were genotyped by polymerase chain reaction sequencing for 15 single nucleotide polymorphisms (SNPs) in the genes IDE, LDLR, APOE, PON1, IGFR1 and IL1B (described in more detail below). Genotyping was accomplished as follows: genomic DNA was extracted from EDTA anti-coagulated venous blood with use of the QIA-amp Blood-DNA mini-reagent set (Qiagen) according to the manufacturer's instructions. DNA was eluted in 200 μL of water in the final step and stored at −20° C. until required. Individual primer sets as described elsewhere herein were used to amplify regions containing the polymorphism of interest. DNA was amplified in 5× buffer [300 mMTris-HCl, pH 9.0, 62.5 mM $(NH_4)_2SO_4$], 2 mM $MgCl_2$, four dNTPs (dATP, dCTP, dGTP, and dTTP; 250 uM each), 1 U of Ampli-Taq DNA polymerase, and 8 pmol each of primers in a final volume of 20 uL. Samples were denatured at 95° C. for 3 min, annealed at 47° C. for 60 s, and elongated at 72° C. for 60 s. This was followed by 35 cycles of denaturation (15 s at 95° C.), annealing (30 s at 47° C.), and extension (20 s at 72° C.). The final cycle was followed by 10 min at 72° C. and 1 min at 25° C. Genotyping was ascertained through direct sequencing of PCR products using the ABI PRISM BigDye Terminator Cycle Sequencing Ready Reaction Kit and analyzed on an ABI PRISM 377 DNA Sequencer (Applied Biosystems, Foster City, Calif., USA).

The presence of IDE_7 or IDE rs2251101 was determined by PCR amplification and sequencing a region of genomic DNA isolated from each patient (a relevant portion of this gene is shown in SEQ ID NO:3). The region amplified contained the polymorphism. PCR was done using standard molecular biology techniques. Primers SEQ ID NO:1 (CAG-CACTTTAGGAGGCCAAG) and SEQ ID NO:2 (CTGC-CCTTACAGGGATGAAA) were used to generate a 682 bp fragment. This fragment was purified and then sequenced using fluorescent sequencing techniques to determined genotype for each patient.

The presence of homozygosity for A for rs2229765 in of insulin-like growth factor 1 receptor precursor (IGFR-1) (a relevant portion of this gene is shown in SEQ ID NO:6) was determined by PCR amplification and sequencing a region of genomic DNA isolated from each patient. The region amplified contained the polymorphism. PCR was done using standard molecular biology techniques. Primers SEQ ID NO:4 (GGCTTAGAGTTCCCCCAAAG) and SEQ ID NO:5 (CTTGCTGATGCCTGTGTTGT) were used to generate a 529 bp fragment. This fragment was purified and then sequenced using fluorescent sequencing techniques to determined genotype for each patient.

The presence of homozygosity for T at IL1B rs1143627 (a relevant portion of this gene is shown in SEQ ID NO:9) as well as the presence of homozygosity for C at IL1B rs16944 (a relevant portion of this gene is shown in SEQ ID NO:10) was detected by PCR amplification and sequencing a region of genomic DNA isolated from each patient. The region amplified contained the polymorphism. PCR was done using standard molecular biology techniques. Primers SEQ ID NO:7 (CACAAAGAGGCAGAGAGACAGA) and SEQ ID NO:8 (GTCTTGCAGGGTTGTGTGAG) were used to generate a 799 bp fragment. This fragment was purified and then sequenced using fluorescent sequencing techniques to determined genotype for each patient.

Genotype LDLR rs2738447 was determined by PCR amplification and sequencing a region of genomic DNA isolated from each patient. The region amplified contained the polymorphism. PCR was done using standard molecular biology techniques. Primers SEQ ID NO:13 and SEQ ID NO:14 were used to generate a 590 bp fragment. This fragment was purified and then sequenced using fluorescent sequencing techniques to determined genotype for each patient.

Genotype LDLR rs7259278 was determined by PCR amplification and sequencing a region of genomic DNA isolated from each patient. The region amplified contained the polymorphism. PCR was done using standard molecular biology techniques. Primers SEQ ID NO:13 and SEQ ID NO:14 were used to generate a 590 bp fragment. This fragment was purified and then sequenced using fluorescent sequencing techniques to determined genotype for each patient.

Genotype LDLR rs11669576 was determined by PCR amplification and sequencing a region of genomic DNA isolated from each patient. The region amplified contained the polymorphism. PCR was done using standard molecular biology techniques. Primers SEQ ID NO:11 (CACCTGGCTGTTTCCTTGAT) and SEQ ID NO:12 (TTCCTGTTCCACCAGTAGGG) were used to generate a 530bp fragment. This fragment was purified and then sequenced using fluorescent sequencing techniques to determined genotype for each patient.

The genotype for LDLR rs1799898 was determined by PCR amplification and sequencing a region of genomic DNA isolated from each patient (a relevant portion of this gene is shown in SEQ ID NO:15). The region amplified contained the polymorphism. PCR was done using standard molecular biology techniques. Primers SEQ ID NO: 13 (GTCACAGGG-GAGGGGTTC) and SEQ ID NO:14 (CTACTGGGGAGC-CTGAGACA) were used to generate a 590 bp fragment. This fragment was purified and then sequenced using fluorescent sequencing techniques to determined genotype for each patient.

The genotype for heterozygosity for Butyrylcholine esterase (BCHE) K variant rs1803274 (a relevant portion of this gene is shown in SEQ ID NO:18) was determined by PCR amplification and sequencing a region of genomic DNA isolated from each patient. The region amplified contained the polymorphism. PCR was done using standard molecular biology techniques. Forward primer was SEQ ID NO: 16 (CAGT-TAATGAAACAGATAAAAATTTT) and reverse primer was SEQ ID NO:17 (CAATATTATCCTTCTGGATT).

Genotypes Apolipoprotein E (APOE) promoter variant rs405509 is determined by PCR amplification and sequencing a region of genomic DNA isolated from each patient (a relevant portion of this gene is shown in SEQ ID NO:21). The region amplified contained the polymorphism. PCR was done using standard molecular biology techniques. Primers SEQ ID NO:19 (GCCTAGCCCCACTTTCTTTT) and SEQ ID NO:20 (AGGTGGGGCATAGAGGTCTT) were used to generate a 587 bp fragment. This fragment was purified and then sequenced using fluorescent sequencing techniques to determined genotype for each patient.

Detection of genotype for Serum paraoxonase/arylesterase 1 (PON1) rs662: determined by PCR amplification and sequencing a region of genomic DNA isolated from each patient. The region amplified contained the polymorphism. PCR was done using standard molecular biology techniques. Primers SEQ ID NO:22 (AAGGCTCCATCCCACATCTT) and SEQ ID NO:23 (TCATCACAGTTCCCCCTCTT) were used to generate a 574 bp fragment. This fragment was purified and then sequenced using fluorescent sequencing techniques to determined genotype for each patient.

For snps the IUPAC-IUB/GCG Ambiguity Codes were used. The table below gives: 1. the ambiguity codes used in DNA sequences 2. which of the four bases (A,C,T,G) are represented by the codes 3. the complement of the ambiguity code

| IUPAC-IUB/GCG Code | Meaning | Complement |
| --- | --- | --- |
| A | A | T |
| C | C | G |
| G | G | C |
| T/U | T | A |
| M | A or C | K |
| R | A or G | Y |
| W | A or T | W |
| S | C or G | S |
| Y | C or T | R |
| K | G or T | M |
| V | A or C or G | B |
| H | A or C or T | D |
| D | A or G or T | H |
| B | C or G or T | V |
| X/N | G or A or T or C | X |
| . | not G or A or T or C | . |

Frequency of Genotypes

Frequency and number of each genotype are shown in Table 1. Note, c refers to an individual who is a c/c homozygote, het refers to a heterozygote for that SNP. Note in some cases an unambiguous genotype could not be assigned and these are represented with a "?" symbol.

TABLE 1

Frequency and counts of genotypes

| Gene | SNP | Genotype | Count | Frequency |
|---|---|---|---|---|
| IL1B | rs1143627 | C | 15 | 0.11719 |
| | | Het | 53 | 0.41406 |
| | | T | 60 | 0.46875 |
| | | Total | 128 | 1 |
| IL1B | rs16944 | C | 60 | 0.46875 |
| | | Het | 53 | 0.41406 |
| | | T | 15 | 0.11719 |
| | | Total | 128 | 1 |
| IGF1R | rs2229765 | A | 19 | 0.14074 |
| | | G | 49 | 0.36296 |
| | | Het | 67 | 0.4963 |
| | | Total | 135 | 1 |
| IGF1R | rs28401726 | C | 109 | 0.80741 |
| | | G | 2 | 0.01481 |
| | | Het | 23 | 0.17037 |
| | | het? | 1 | 0.00741 |
| | | Total | 135 | 1 |
| PON1 | rs662 | a | 61 | 0.45185 |
| | | g | 15 | 0.11111 |
| | | het | 59 | 0.43704 |
| | | Total | 135 | 1 |
| LDLR 13 | rs7259278 | g | 101 | 0.77692 |
| | | het | 25 | 0.19231 |
| | | t | 4 | 0.03077 |
| | | Total | 130 | 1 |
| LDLR 13 | rs2738447 | a | 24 | 0.18462 |
| | | c | 44 | 0.33846 |
| | | het | 62 | 0.47692 |
| | | Total | 130 | 1 |
| LDLR 13 | rs1799898 | c | 87 | 0.66923 |
| | | het | 34 | 0.26154 |
| | | het? | 7 | 0.05385 |
| | | t | 2 | 0.01538 |
| | | Total | 130 | 1 |
| LDLR 13 | rs688 | c | 46 | 0.34848 |
| | | het | 62 | 0.4697 |
| | | t | 24 | 0.18182 |
| | | Total | 132 | 1 |
| LDLR 13 | snp 5 | c | 127 | 0.96212 |
| | | het | 5 | 0.03788 |
| | | Total | 132 | 1 |
| IDE | rs2251101 | c | 16 | 0.11765 |
| | | het | 53 | 0.38971 |
| | | t | 67 | 0.49265 |
| | | Total | 136 | 1 |
| LDLR 8 | rs11669576 | g | 123 | 0.90441 |
| | | het | 13 | 0.09559 |
| | | Total | 136 | 1 |
| BUCHE | rs1803274 | a | 3 | 0.02239 |
| | | g | 85 | 0.63433 |
| | | het | 46 | 0.34328 |
| | | Total | 134 | 1 |
| APOE | rs449647 | a | 88 | 0.70968 |
| | | e? | 1 | 0.00806 |
| | | het | 29 | 0.23387 |
| | | t | 6 | 0.04839 |
| | | Total | 124 | 1 |
| APOE | rs405509 | g | 21 | 0.16935 |
| | | het | 56 | 0.45161 |
| | | t | 47 | 0.37903 |
| | | Total | 124 | 1 |
| APOE | −427 | het | 13 | 0.10484 |
| | | t | 111 | 0.89516 |
| | | Total | 124 | 1 |

Genotype Frequency

The frequency of each polymorphism was examined relative to data published in the HapMap project (www.hapmap.org). In some cases HapMap data was not available and other databases were used, such as the DECODE database. The HapMap database is based on a relatively small sampling of humans from different geographical locations around the globe. There are four main groups of people. The first group is individuals from the Yoruba people of Ibidan Peninsula in Nigeria (referred to as YRI). The second group is from the CEPH project in Utah, exclusively Americans of European ancestry (referred to as CEU). The third group is composed of individuals from the Han Chinese population of Beijing (referred to as CHB). The fourth group is composed of unrelated individuals of Japanese ancestry from the Tokyo area (referred to as JPT).

In most cases frequencies found in the KET-04-001 study agreed with published frequencies from a European American population from Utah. In study KET-04-001, 94.5% of subjects reported themselves as Caucasian/white, 4.8% Hispanic and 0.7% Black.

In some cases the frequencies differed. For example, the frequency of the IDE rs2251101 C/C genotype was quite low in the HapMap database (0.0314) and considerably higher in the KET-01-004 study (0.117). The higher frequency of the c/c genotype in the KET-04-001 study is probably a due to Accera's study utilizing an AD population. The C/C genotype has been identified in some studies as a risk factor for AD. In addition, ApoE promoter polymorphisms differ slightly in the KET-04-001 population compared to random European sampling. This is also consistent with the well know association of ApoE and AD.

Study Population

One hundred fifty-two subjects were randomized in this study. 140 subjects completed at least one follow-up visit subsequent to Baseline, these subjects comprise the ITT population used for efficacy analyses. Treatment groups were well balanced for baseline characteristics. One-hundred thirty-five subjects (n=75 AC; n=60 PL) consented to genotyping for the APOE locus.

Ketosis

BHB levels were determined at Screening (pre-dose), Baseline, Day 45, Day 90 (pre and post-dose) and Day 104 (pre-dose). Post-dose levels were measured two hours after administration of investigational product. Screening BHB levels were within normal ranges and did not differ between treatment groups (0.11±0.08 mM AC; 0.12±0.11 mM PL, p=0.590). Two hour post-dose, AC-1202 induced a significant elevation in serum BHB levels on visit days Baseline, Day 45 and Day 90. At Baseline, subjects received ½ dose of AC-1202 and mean serum BHB increased from 0.07 mM to 0.14 mM, which was significantly different from the Placebo group (p<0.0001). Higher levels of BHB were obtained on full dose. Average 2-hour post-dose BHB values in the AC-1202 group were 0.36 mM on Day 45 and 0.39 mM on Day 90, both significantly different from Placebo group (p<0.0001). BHB levels were not different between AC-1202 and Placebo groups at any pre-dose sampling or after the 14 day washout.

ADAS-Cog

When ADAS-Cog scores were evaluated at Day 45 in the ITT population with LOCF, there was a significant effect of AC-1202 treatment on change' from Baseline in ADAS-Cog scores. Subjects treated with AC-1202 showed a mean change from Baseline of −0.177 points (negative score represents an improvement over Baseline), while those treated with Placebo showed a mean change of 1.73 points (p=0.024). At Day 90, AC-1202 led to a mean −0.31 point change from Baseline in ADAS-Cog, whereas the Placebo group showed a mean 1.23 point change (p=0.077). On Day 104, after the two week Washout, there was no difference in the ITT population between treatment groups (p=0.405).

Genotype Effects on ADAS-Cog

Genetic influence of ketone body treatment was examined for a series of genetic markers in correlation with Day 90 change from Baseline in ADAS-Cog. Analysis of the ADAS-Cog scores revealed that the carriage status of several of the markers tested demonstrated increased efficacy to AC-1202 treatment (See table 2).

IDE rs2551101. Subjects who were heterozygous at the rs2551101 locus demonstrated a 4.06 point improvement in ADAS-Cog score when compared to placebo (p=0.0068). Subjects who were not homozygous for the C allele demonstrated a 2.74 point improvement in ADAS-Cog when compared to placebo (p=0.0059).

IL1B rs1143627. Subjects who were homozygous for the T allele demonstrated a 3.5 point improvement in ADAS-Cog when compared to placebo (p=0.0145).

IL1B rs16944. Subjects who were homozygous for the C allele demonstrated a 3.5 point improvement in ADAS-Cog when compared to placebo (p=0.00145).

IGF1R rs229765. Subjects who were homozygous for the A allele demonstrated a 7.3 point improvement in ADAS-Cog when compared to placebo (p=0.0072).

IGF1R rs28401726. No significant effects were noted with this allele.

PON1 rs662. No significant effects were noted with this allele.

LDLR rs7259278. Subjects who were homozygous for the G allele demonstrated a 2.56 point improvement in ADAS-Cog when compared to placebo (p=0.0236).

LDLR rs2738447. Subjects who were homozygous for the C allele demonstrated a 3.51 point improvement in ADAS-Cog when compared to placebo (p=0.037).

LDLR rs1799898. Subjects who were homozygous for the C allele demonstrated a 2.44 point improvement in ADAS-Cog when compared to placebo (p=0.045).

LDLR rs11669576. No significant effects were noted with this allele.

BUCHE rs1803274. Subjects who were heterozygous at the rs1803274 locus demonstrated a 4.29 point improvement in ADAS-Cog score when compared to placebo (p=0.0133).

APOE rs448647. No significant effects were noted with this allele.

APOE rs405509. Subjects who were heterozygous at the rs405509 locus demonstrated a 3.68 point improvement in ADAS-Cog score when compared to placebo (p=0.0085).

APOE rs769446. No significant effects were noted with this allele.

TABLE 2

Treatment by Genotype
Change in ADAS-Cog From Baseline at Day 90

| Snp | Genotype | N for AC-1202 | N for Placebo | 2-way Anova Treatment*Genotype P-value |
|---|---|---|---|---|
| APOE rs449647 | a | 39 | 38 | 0.147 |
|  | Het | 17 | 11 | 0.14 |
|  | t | 3 | 3 | 0.4 |
| APOE rs405509 | g | 11 | 7 | 0.48 |
|  | Het | 26 | 27 | 0.0085 |
|  | t | 23 | 18 | 0.629 |
| APOE rs769446 | Het | 5 | 6 | 0.405 |
|  | t | 55 | 46 | 0.0951 |
| BUCHE rs1803274 | a | 2 |  | Na |
|  | g | 40 | 39 | 0.541 |
|  | Het | 25 | 15 | 0.0133 |
| IDE rs2251101 | c | 9 | 7 | 0.079 |
|  | Het | 22 | 25 | 0.0068 |
|  | t | 36 | 24 | 0.266 |
| IGF1R rs2229765 | A | 5 | 13 | 0.00719 |
|  | G | 27 | 18 | 0.156 |
|  | het | 34 | 25 | 0.826 |
| IGF1R rs28401726 | C | 52 | 48 | 0.0578 |
|  | het | 14 | 5 | 0.901 |
|  | G |  | 2 | Na |
| IL1B rs16944 | C | 29 | 27 | 0.0145 |
|  | het | 28 | 17 | 0.845 |
|  | T | 6 | 9 | 0.479 |
| IL1B rs1143627 | C | 6 | 9 | 0.479 |
|  | het | 28 | 17 | 0.845 |
|  | T | 29 | 27 | 0.0145 |
| LDLR8 rs11669576 | G | 59 | 51 | 0.025 |
|  | het | 8 | 5 | 0.458 |
| LDLR13 rs688 | C | 24 | 22 | 0.987 |
|  | het | 33 | 20 | 0.061 |
|  | T | 7 | 13 | 0.061 |
| LDLR13 rs2738447 | A | 13 | 11 | 0.77 |
|  | C | 18 | 21 | 0.037 |
|  | het | 32 | 22 | 0.176 |
| LDLR13 rs7259278 | G | 44 | 44 | 0.0236 |
|  | het | 17 | 8 | 0.403 |
|  | T | 2 | 2 | 0.974 |
| LDLR 13 rs1799898 | C | 40 | 35 | 0.045 |
|  | het | 18 | 15 | 0.126 |
|  | T | 1 | 1 | 0.819 |
| PON1 rs662 | A | 28 | 26 | 0.12 |
|  | G | 6 | 7 | 0.239 |
|  | het | 32 | 23 | 0.73 |
| IDE rs2251101 | c/c | 9 | 7 | 0.079 |
|  | other | 58 | 49 | 0.0059 |

AI program source: phg Tab 3

ADCS-CGIC and MMSE

When comparing AC-1202 and Placebo in the ITT population using LOCF, AC-1202 did not lead to a significant difference in the distribution on ADCS-CGIC scores at any study.

TABLE 2

Treatment by Genotype: ADCS-CGIC Score at Day 90

| Snp | genotype | N for Ketasyn | N for Placebo | 2-way Anova Treatment*Genotype Pvalue |
|---|---|---|---|---|
| Apoe4 | 0 | 29 | 26 | 0.218 |
|  | 1 | 39 | 31 | 0.769 |
| APOE rs449647 | a | 39 | 38 | 0.201 |
|  | het | 17 | 11 | 0.604 |
|  | t | 3 | 3 | 0.796 |
| APOE rs405509 | g | 11 | 7 | 0.6868 |
|  | het | 26 | 27 | 0.5660 |
|  | t | 23 | 18 | 0.7090 |

TABLE 2-continued

Treatment by Genotype: ADCS-CGIC Score at Day 90

| Snp | geno-type | N for Ketasyn | N for Placebo | 2-way Anova Treatment*Genotype Pvalue |
|---|---|---|---|---|
| APOE rs769446 | het | 5 | 6 | 0.441 |
| | t | 55 | 46 | 0.274 |
| BUCHE rs1803274 | a | 2 | | Na |
| | g | 40 | 39 | 0.356 |
| | het | 25 | 15 | 0.574 |
| IDE rs2251101 | c | 9 | 7 | 0.789 |
| | het | 22 | 25 | 0.569 |
| | t | 36 | 24 | 0.259 |
| IGF1R rs2229765 | a | 5 | 13 | 0.350 |
| | g | 27 | 18 | 0.871 |
| | het | 34 | 25 | 0.585 |
| IGF1R rs28401726 | c | 52 | 48 | 0.299 |
| | het | 14 | 5 | 0.292 |
| | g | | 2 | Na |
| IL1B rs16944 | c | 29 | 27 | 0.839 |
| | het | 28 | 17 | 0.492 |
| | t | 6 | 9 | 0.437 |
| IL1B rs1143627 | c | 6 | 9 | 0.437 |
| | het | 28 | 17 | 0.492 |
| | t | 29 | 27 | 0.839 |
| LDLR8 rs11669576 | g | 59 | 51 | 0.538 |
| | het | 8 | 5 | 0.935 |
| LDLR13 rs688 | c | 24 | 22 | 0.436 |
| | het | 33 | 20 | 0.662 |
| | t | 7 | 13 | 0.295 |
| LDLR13 rs2738447 | a | 13 | 11 | 0.635 |
| | c | 18 | 21 | 0.993 |
| | het | 32 | 22 | 0.147 |
| LDLR13 rs7259278 | g | 44 | 44 | 0.288 |
| | het | 17 | 8 | 0.552 |
| | t | 2 | 2 | 1 |
| LDLR13 rs1799898 | c | 40 | 35 | 0.175 |
| | het | 18 | 15 | 0.986 |
| | t | 1 | 1 | 0.321 |
| PON1 rs662 | a | 28 | 26 | 0.408 |
| | g | 6 | 7 | 0.975 |
| | het | 32 | 23 | 0.722 |
| IDE rs2251101 | c/c | 9 | 7 | 0.494 |
| | other | 58 | 49 | 0.790 |

AI program source: phg Tab 5

Significant treatment effects were found in change from Baseline in MMSE in Carriers of APOE rs405509 and PON1 rs662

TABLE 3

Treatment by Genotype: Change in MMSE From Baseline at Day 90

| Snp | Geno-type | N for Ketasyn | N for Placebo | 2-way Anova Treatment*Genotype P-value |
|---|---|---|---|---|
| Apoe4 | 0 | 29 | 26 | 0.369 |
| | 1 | 39 | 31 | 0.704 |
| APOE rs449647 | A | 39 | 38 | 0.595 |
| | het | 17 | 11 | 0.424 |
| | T | 3 | 3 | 0.277 |
| APOE rs405509 | G | 11 | 7 | 0.929 |
| | het | 26 | 27 | 0.067 |
| | T | 23 | 18 | 0.037 |
| APOE rs769446 | het | 5 | 6 | 0.504 |
| | T | 55 | 46 | 0.834 |
| BUCHE rs1803274 | A | 2 | | Na |
| | G | 40 | 39 | 0.892 |
| | het | 25 | 15 | 0.413 |
| IDE rs2251101 | C | 9 | 7 | 0.908 |
| | het | 22 | 25 | 0.206 |
| | T | 36 | 24 | 0.111 |

TABLE 3-continued

Treatment by Genotype: Change in MMSE From Baseline at Day 90

| Snp | Geno-type | N for Ketasyn | N for Placebo | 2-way Anova Treatment*Genotype P-value |
|---|---|---|---|---|
| IGF1R rs2229765 | A | 5 | 13 | 0.125 |
| | G | 27 | 18 | 0.929 |
| | het | 34 | 25 | 0.844 |
| IGF1R rs28401726 | C | 52 | 48 | 0.392 |
| | het | 14 | 5 | 0.254 |
| | G | | 2 | Na |
| IL1B rs16944 | C | 29 | 27 | 0.846 |
| | het | 28 | 17 | 0.943 |
| | T | 6 | 9 | 0.879 |
| IL1B rs1143627 | C | 6 | 9 | 0.879 |
| | het | 28 | 17 | 0.943 |
| | T | 29 | 27 | 0.846 |
| LDLR8 rs11669576 | G | 59 | 51 | 0.756 |
| | het | 8 | 5 | 0.762 |
| LDLR13 rs688 | C | 24 | 22 | 0.240 |
| | het | 33 | 20 | 0.365 |
| | T | 7 | 13 | 0.468 |
| LDLR13 rs2738447 | A | 13 | 11 | 0.709 |
| | C | 18 | 21 | 0.265 |
| | het | 32 | 22 | 0.513 |
| LDLR13 rs7259278 | G | 44 | 44 | 1 |
| | het | 17 | 8 | 0.903 |
| | T | 2 | 2 | 0.859 |
| LDLR 13 rs1799898 | C | 40 | 35 | 0.322 |
| | het | 18 | 15 | 0.145 |
| | T | 1 | 1 | 0.799 |
| PON1 rs662 | A | 28 | 26 | 0.085 |
| | G | 6 | 7 | 0.031 |
| | het | 32 | 23 | 0.287 |
| IDE rs2251101 | c/c | 9 | 7 | 0.682 |
| | other | 58 | 49 | 0.909 |

AI program source: phg Tab 4

Adverse Events Occurring before and after a Change in Dosing Protocol

During the first several months of the study, it appeared that a relatively high number of subjects were withdrawing from the study due to gastro-intestinal adverse events, in particular, for diarrhea and flatulence. Following an assessment of the reasons given for discontinuation, it was recommended that study medication or placebo should be mixed with a high protein drink (Ensure™) in order to improve investigational product tolerability. Clinical sites were informed of this decision and were subsequently provided with an ample supply of Ensure for distribution to study subjects. Although specific data were not collected regarding which subjects adhered to the new medication mixing instructions, Accera had reason to believe that Ensure™ was made available to all subjects who were on-study at that point in time or enrolled after the change.

To evaluate whether or not this change in study medication mixing instructions appeared to improve product tolerability, an analysis of subject discontinuations was undertaken before and after the change was undertaken.

Discontinuations Prior to the Change

Ten subjects [9 of 31 (29.0%) Treatment and 1 of 27 (3.4%) placebo] discontinued the study. During this time period, events within the gastro-intestinal system were the leading cause for withdrawal from the study. Within the GI system, 7 of 31 (22.6%) Treatment subjects and 1 of 27 (3.4%) placebo subjects discontinued the study due to one or more adverse events.

Discontinuations after the Change

Following the change in medication mixing instructions, the overall incidence of adverse events leading to study discontinuation declined slightly in the Treatment group from 29.0% to 21.9%. Most notably, the incidence of gastro-intestinal events causing study withdrawal in the Treatment group declined from 22.6% to 12.5%.

Although the incidence of AEs leading to discontinuation declined in Treatment subjects after the change, the overall incidence of all reported AEs did not decline after this date. Twenty-one of 31 (67.7%) Treatment subjects and 13 of 27 (48.1%) placebo subjects experienced at least one AE prior to the change. After the change, 47 of 64 (73.4%) Treatment subjects and 29 of 49 (59.2%) placebo experienced one or more adverse events (data not shown).

All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of treatment for Alzheimer's disease, comprising the steps of:
   a. selecting a human patient having, or at risk of Alzheimer's disease;
   b. determining in the patient the presence of at least one of the specific genotypes selected from the group consisting of:
      i. heterozygosity for C/T for Insulin Degrading Enzyme (IDE) rs 2251101 at relevant portion shown by SEQ ID NO:3, and
      ii. absence of homozygosity for C/C of IDE rs 2251101 at relevant portion shown by SEQ ID NO:3; and
   administering to the patient having at least one of the specific genotypes in (b a composition comprising an effective amount of medium chain triglycerides (MCT) of the formula:

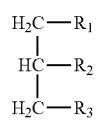

wherein the R1, R2, and R3 esterified to the glycerol backbone are each independently fatty acids having 5-12 carbon chains.

2. The method of claim 1, wherein the method further comprises testing the patient for the absence of ApoE4 genotype.

3. The method of claim 1, wherein the composition is an oral composition which further comprises glucose.

4. The method of claim 1, wherein the composition is administered in an amount effective to raise the blood level of D-beta-hydroxybutyrate in the patient from about 0.1 mM to about 50 mM.

5. The method of claim 1, wherein the composition is administered in an amount effective to raise the blood level of D-beta-hydroxybutyrate in the patient from about 0.2 mM to about 5 mM.

6. The method of claim 1, wherein the composition is administered at a dose of about 0.05 g/kg/day to about 10 g/kg/day.

* * * * *

SEQUENCE LISTING

```
<160> NUMBER OF SEQ ID NOS: 25

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
cagcacttta ggaggccaag                                                    20

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
ctgcccttac agggatgaaa                                                    20

<210> SEQ ID NO 3
<211> LENGTH: 701
<212> TYPE: DNA
<213> ORGANISM: Homo sapiens
<220> FEATURE:
<221> NAME/KEY: misc_feature
<223> OTHER INFORMATION: Y  is c or t

<400> SEQUENCE: 3
ctattactac aggaaatcca catggtacaa tgagatctaa agtccaaaga gctgagtgga         60
ggtttgaatc tgcttcctgg atgatcctgg gcaaactatt cagcctttct gagcctattt        120
ccacctctga aaatctggga tgatgaaatt ttttatcact atcctccctg ttgaaagact        180
gtgggctggg tgcagtggct catgcctgta atcccagcac tttaggaggc caaggcgggt        240
ggatcacctg aggtcaggag tttgagacca gcctggccaa catggcaaaa ctccatctct        300
actaaaaata caaaaaatta gtagagcgca gtggcgcgca caggtaatcc cagctactcc        360
agaggctgag gcaggagaat cgctggaacc caggaggcgg gggttgcagt gagccaagat        420
cgcacgactg cactgtagcc tggctgacag agcgagactc tgtctcaaaa aaaaacaaaa        480
acaaaaaccc taaaaaacaa yaggggggacc tgctgagtcc cctgagtccc tccatgtatc        540
atgaatgaga ggacgactgt cccaactcat aaatcctgga gttgctctgt tgctcttggc        600
ctctgtgtgg ggctgccaca tcgtccctga gaacaatgct gactgtgcgg gctggaccac        660
tgtcctatgc tggaaaagtg aggaacaagc agattcctct t                           701
```

```
<210> SEQ ID NO 4
<211> LENGTH: 20
<212> TYPE: DNA
<213> ORGANISM: Artificial
<220> FEATURE:
<223> OTHER INFORMATION: Synthetic

<400> SEQUENCE: 4
ggcttagagt tcccccaaag                                                   20

<210> SEQ ID NO 5
<211> LENGTH: 20
<212> TYPE: DNA
<213> ORGANISM: Artificial
<220> FEATURE:
<223> OTHER INFORMATION: Synthetic

<400> SEQUENCE: 5
cttgctgatg cctgtgttgt                                                   20

<210> SEQ ID NO 6
<211> LENGTH: 529
<212> TYPE: DNA
<213> ORGANISM: Homo sapiens
<220> FEATURE:
<221> NAME/KEY: misc_feature
<223> OTHER INFORMATION: R is g or a
<220> FEATURE:
<221> NAME/KEY: misc_feature
<223> OTHER INFORMATION: Y is c or t

<400> SEQUENCE: 6
gggcttgttt ctgtacctgc tttaattacg gtttcttctc cagtgtacgt tcctgatgag       60
tgggaggtgg ctcgggagaa gatcaccatg agccgggaac ttgggcaggg gtcgtttggg      120
atggtctatg aaggagttgc caagggtgtg gtgaaagatg aacctgaaac cagagtggcc      180
attaaaacag tgaacgaggc cgcaagcatg cgtgaraggg ttgagtttct caacgaagct      240
tctgtgatga aggagttcaa ttgtcaccat gtggtaagag aaagttcctg aaaagycaaa      300
atgcagcaca gggagagggt atcacacaag cctcccagta tgttcttggc tgcatgtacc      360
cgtgggtttg gtgtcttgcc tttgccttct ggatagttac cccattacct cactgctacc      420
ttcagacccc tgtgctcaga ccaggccgca gcaccacaga gacagttcca gacaacacag      480
gcaycagcaa gggccacctg accctctgag tctttctctt tttgattcc                  529

<210> SEQ ID NO 7
<211> LENGTH: 22
<212> TYPE: DNA
<213> ORGANISM: Artificial
<220> FEATURE:
<223> OTHER INFORMATION: Synthetic

<400> SEQUENCE: 7
cacaaagagg cagagagaca ga                                                22

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
gtcttgcagg gttgtgtgag                                                   20
```

<210> SEQ ID NO 9
<211> LENGTH: 602
<212> TYPE: DNA
<213> ORGANISM: Homo sapiens
<220> FEATURE:
<221> NAME/KEY: misc_feature
<223> OTHER INFORMATION: Y is c or t

<400> SEQUENCE: 9

```
cccacaccct caatacagac agggagggct attggcccctt cattgtaccc atttatccat    60
ctgtaagtgg gaagattcct aaacttaagt acaaagaagt gaatgaagaa aagtatgtgc   120
atgtataaat ctgtgtgtct tccactttgt cccacatata ctaaatttaa acattcttct   180
aacgtgggaa aatccagtat tttaatgtgg acatcaactg cacaacgatt gtcaggaaaa   240
caatgcatat ttgcatggtg atacatttgc aaaatgtgtc atagtttgct actccttgcc   300
cttccatgaa ccagagaatt atctcagttt attagtcccc tccctaaga agcttccacc   360
aatactcttt tccccttcc tttaacttga ttgtgaaatc aggtattcaa cagagaaatt   420
tctcagcctc ctacttctgc ttttgaaagc yataaaaaca gcgagggaga aactggcaga   480
taccaaacct cttcgaggca caaggcacaa caggctgctc tgggattctc ttcagccaat   540
cttcattgct caagtatgac tttaatcttc cttacaacta ggtgctaagg gagtctctct   600
gt                                                                  602
```

<210> SEQ ID NO 10
<211> LENGTH: 593
<212> TYPE: DNA
<213> ORGANISM: Homo sapiens
<220> FEATURE:
<221> NAME/KEY: misc_feature
<223> OTHER INFORMATION: R is a or g

<400> SEQUENCE: 10

```
cagatttata catgcacata cttttcttca ttcacttctt tgtacttaag tttaggaatc    60
ttcccactta cagatggata aatgggtaca atgaagggcc aatagccctc cctgtctgta   120
ttgagggtgt gggtctctac cttgggtgct gttctctgcc tcrggagctc tctgtcaatt   180
gcaggagcct ctgaggagaa aattgacctt tcttggctgg ggcagagaac atacggtatg   240
cagggttcag gctcctgacg gagttggggc aaccctggag ataagctcac acaaccctgc   300
aagaccaggt gctgttaccc tagccaatct catggatgaa ccagatcaat gccagatgag   360
ctctgcctaa aatgattttt tggtgaactc tgaaaagtgg aatattgttt ctgtaagaat   420
atccatctga gactctatct cttggtaata ccaagagtta tcagtttctc tttaaccgag   480
acaccagcaa agtgcctgct ccagggtact gcccagggga gccctccatt tgtagaatga   540
atgagagtcc aggttatgaa cagtgcctgg agtgtaggaa caccctcctt tgc          593
```

<210> SEQ ID NO 11
<211> LENGTH: 20
<212> TYPE: DNA
<213> ORGANISM: Artificial
<220> FEATURE:
<223> OTHER INFORMATION: Synthetic

<400> SEQUENCE: 11

```
cacctggctg tttccttgat                                                20
```

<210> SEQ ID NO 12

```
<211> LENGTH: 20
<212> TYPE: DNA
<213> ORGANISM: Artificial
<220> FEATURE:
<223> OTHER INFORMATION: Synthetic

<400> SEQUENCE: 12
ttcctgttcc accagtaggg                                                   20

<210> SEQ ID NO 13
<211> LENGTH: 18
<212> TYPE: DNA
<213> ORGANISM: Artificial
<220> FEATURE:
<223> OTHER INFORMATION: Synthetic

<400> SEQUENCE: 13
gtcacagggg aggggttc                                                     18

<210> SEQ ID NO 14
<211> LENGTH: 20
<212> TYPE: DNA
<213> ORGANISM: Artificial
<220> FEATURE:
<223> OTHER INFORMATION: Synthetic

<400> SEQUENCE: 14
ctactgggga gcctgagaca                                                   20

<210> SEQ ID NO 15
<211> LENGTH: 201
<212> TYPE: DNA
<213> ORGANISM: Homo sapiens
<220> FEATURE:
<221> NAME/KEY: misc_feature
<223> OTHER INFORMATION: Y is c or t

<400> SEQUENCE: 15
cggagcagcg tggccaggcc ctcaggaccc tctgggactg gcatcagcac gtgacctctc        60
cttatccact tgtgtgtcta gatctcctca gtggccgcct ytactgggtt gactccaaac       120
ttcactccat ctcaagcatc gatgtcaacg ggggcaaccg gaagaccatc ttggaggatg       180
aaaagaggct ggcccacccc t                                                201

<210> SEQ ID NO 16
<211> LENGTH: 26
<212> TYPE: DNA
<213> ORGANISM: Artificial
<220> FEATURE:
<223> OTHER INFORMATION: Synthetic

<400> SEQUENCE: 16
cagttaatga aacagataaa aatttt                                            26

<210> SEQ ID NO 17
<211> LENGTH: 20
<212> TYPE: DNA
<213> ORGANISM: Artificial
<220> FEATURE:
<223> OTHER INFORMATION: Synthetic

<400> SEQUENCE: 17
caatattatc cttctggatt                                                   20

<210> SEQ ID NO 18
```

```
<211> LENGTH: 401
<212> TYPE: DNA
<213> ORGANISM: Homo sapiens
<220> FEATURE:
<221> NAME/KEY: misc_feature
<223> OTHER INFORMATION: R is g or a

<400> SEQUENCE: 18
tctgtaaaga ttttattaaa atctcttttc aggcaaagcg agctaataac aaataataaa      60
gaataaataa agaaaataat gctgtactgt gtagttagag aaaatggctt ttgtattcga     120
aattattttt cagttaatga aacagataaa aattttgatt aatacaactt attccatatt     180
ttacaggaaa tattgatgaa rcagaatggg agtggaaagc aggattccat cgctggaaca     240
attacatgat ggactggaaa aatcaattta acgattacac tagcaagaaa gaaagttgtg     300
tgggtctcta attaatagat ttacccttta tagaacatat tttcctttag atcaaggcaa     360
aaatatcagg agcttttta cacacctact aaaaaagtta t                         401

<210> SEQ ID NO 19
<211> LENGTH: 20
<212> TYPE: DNA
<213> ORGANISM: Artificial
<220> FEATURE:
<223> OTHER INFORMATION: Synthetic

<400> SEQUENCE: 19
gcctagcccc actttctttt                                                 20

<210> SEQ ID NO 20
<211> LENGTH: 20
<212> TYPE: DNA
<213> ORGANISM: Artificial
<220> FEATURE:
<223> OTHER INFORMATION: Synthetic

<400> SEQUENCE: 20
aggtggggca tagaggtctt                                                 20

<210> SEQ ID NO 21
<211> LENGTH: 1393
<212> TYPE: DNA
<213> ORGANISM: Homo sapiens
<220> FEATURE:
<221> NAME/KEY: misc_feature
<223> OTHER INFORMATION: M is a or c

<400> SEQUENCE: 21
acttgtccaa ttatagggct ccccctgtcc cgcccctcc cccagggata gggcgggctg       60
ggccagcccc cagtcacgag gtgggctgtt ctcccctgc cccaggcaca gcagggcaga     120
gggaggaagg aggtggggca tagaggtctt ttgaccaccc ccacagtcc ccaggaaggg     180 aggacacctc gcccagtaat mcagacaccc tcctccattc tggggccaa gcgtggaagg     240 ggaatgtgga ggctgccgcc cagagtcctc ctttcctgac cctgtccttt cctgtgcctg     300
gatgaatgta atctggagag ggggctgggg atctggactc ctggatccca gaaagaaagt     360
agggctaggg ggctggacag aagtgggatg ggaggggctg gggcggtag ctcacgcctg     420 taatcccagc actttgggag gccacagtgg gcgaatcact taaggtcagg agtttgagac     480
cagcctggcc aacatggtga aaccccatct ctactaaaaa tacaaaagtt agccaggcgt     540
ggtggcgggc gcctgtaatc ctagctactt gggaggctga ggcaggagaa tcgcttgaac     600
ccgggaggcg gaggttacag tgagccgaga tctcgccact gcactccagc ctcagcaaga     660
```

```
gggagactgt ctcaaaaaaa gaaaaaaaag aaagtggggc taggcggctg gacagaagtg      720
ggatgggagg ggtgggaaca gtatgatgca cctgctaaaa gtcgaggctt tgcaaatggg      780
acctgggttt taatcacagc ttcctctttg gttgtgacct tgagcacagg ggagcccccct     840 ccccacatgt gaaatgagat tccagcacct cccctggct gccacaggta ttgtggtttc       900
caggggcttg aagccgtgct tctgggttaa ggttaggatt ctggagtcaa attgccaggg      960
cgtgaatcct ggctctgcca gttgccagct gtgtgacctt gggcaaatga cttgtcctct     1020
ctgagcatca agttcctttg ctcatcagac tgggaaagca gcggcacggg tatgtttggt     1080
gacaagctaa cgtgtattga gcatggagga cagcccggc acacagcggt cctatgttag      1140
ggctagcaat ggacaggcca cagtgaacgc tcagacgctg tcactttcct aagccctgtt    1200
ataaatccca gatgtttcag aggagaaacc cgtggttcag cagcaagacg aatggcaaaa    1260
ccacacagtg agaactggga gagactggga ctcattcctg gctcctggag cgggtgggat    1320
cagaagattc tgcgggtcag gggaggctga actcctggtt cgagaaggaa cccccagtgc    1380
cgggccgggc ctg                                                        1393

<210> SEQ ID NO 22
<211> LENGTH: 20
<212> TYPE: DNA
<213> ORGANISM: Artificial
<220> FEATURE:
<223> OTHER INFORMATION: Synthetic

<400> SEQUENCE: 22
aaggctccat cccacatctt                                                   20

<210> SEQ ID NO 23
<211> LENGTH: 20
<212> TYPE: DNA
<213> ORGANISM: Artificial
<220> FEATURE:
<223> OTHER INFORMATION: Synthetic

<400> SEQUENCE: 23
tcatcacagt tccccctctt                                                   20

<210> SEQ ID NO 24
<211> LENGTH: 701
<212> TYPE: DNA
<213> ORGANISM: Homo sapiens
<220> FEATURE:
<221> NAME/KEY: misc_feature
<223> OTHER INFORMATION: M is a or c

<400> SEQUENCE: 24
tgctccctga aggtttccct ctttcttttc tttgtttttt cttttttga gatgaggtct        60 tggtctgtca cccaggctgg agtgcactgg cgcaatcgta gctcactgca gcctccacct      120
cccaggctca agtgatcctc ctgcctcacc ctcctgagta gctgagatta cagacacgtg      180
ccaccacggc agactaattt tattttattt ttgggaagag acaaagtctt gttatgttgg      240
cctggctggt ctcaaactca gggtgcaagc gatcctcccg cctcagcctt ccaaactgct      300
gggattacag gcgtgggcca ccgtacccag cctccttgaa gttttctga cctgcaactc       360 ccctacctgc ccattggaga gggcgtcaca ggggaggggt tcaggctcac atgtggttgg     420
agctgcctct ccaggtgctt ttctgctagg tccctggcag ggggtcttcc tgcccggagc      480
agcgtggcca ggccctcagg mccctctggg actggcatca gcacgtgacc tctccttatc      540
```

```
cacttgtgtg tctagatctc ctcagtggcc gcctctactg ggttgactcc aaacttcact    600
ccatctcaag catcgatgtc aacgggggca accggaagac catcttggag gatgaaaaga    660
ggctggccca ccccttctcc ttggccgtct ttgaggtgtg g                       701

<210> SEQ ID NO 25
<211> LENGTH: 801
<212> TYPE: DNA
<213> ORGANISM: Homo sapiens
<220> FEATURE:
<221> NAME/KEY: misc_feature
<223> OTHER INFORMATION: K is g or t

<400> SEQUENCE: 25
ctggcgcaat cgtagctcac tgcagcctcc acctcccagg ctcaagtgat cctcctgcct     60
caccctcctg agtagctgag attacagaca cgtgccacca cggcagacta attttatttt    120 attttggga  agagacaaag tcttgttatg ttggcctggc tggtctcaaa ctcagggtgc    180
aagcgatcct cccgcctcag ccttccaaac tgctgggatt acaggcgtgg gccaccgtac    240
ccagcctcct tgaagttttt ctgacctgca actccctac  ctgcccattg gagagggcgt    300 cacagggag  gggttcaggc tcacatgtgg ttggagctgc ctctccaggt gcttttctgc    360
taggtccctg gcaggggtc  ttcctgcccg gagcagcgtg kccaggccct caggaccctc    420
tgggactggc atcagcacgt gacctctcct tatccacttg tgtgtctaga tctcctcagt    480
ggccgcctct actgggttga ctccaaactt cactccatct caagcatcga tgtcaacggg    540
ggcaaccgga agaccatctt ggaggatgaa aagaggctgg cccacccctt ctccttggcc    600
gtctttgagg tgtggcttac gtacgagatg caagcactta ggtggcggat agacacagac    660
tatagatcac tcaagccaag atgaacgcag aaaactggtt gtgactagga ggaggtctta    720
gacctgagtt atttctattt tcttctttct ttttttttt  tttttgaga cagagttttg    780 ctctcgtttc ccaggctgga g                                             801
```